United States Patent
Sawada et al.

(10) Patent No.: US 10,467,750 B2
(45) Date of Patent: Nov. 5, 2019

(54) DISPLAY CONTROL APPARATUS, DISPLAY CONTROL METHOD, AND RECORDING MEDIUM

(71) Applicant: Panasonic Intellectual Property Management Co., Ltd., Osaka (JP)

(72) Inventors: Yoshihide Sawada, Tokyo (JP); Yoshikuni Sato, Osaka (JP); Toru Nakada, Kanagawa (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 16/034,426

(22) Filed: Jul. 13, 2018

(65) Prior Publication Data

US 2019/0026890 A1 Jan. 24, 2019

(30) Foreign Application Priority Data

Jul. 21, 2017 (JP) .................................. 2017-141423

(51) Int. Cl.
```
G06T 3/40        (2006.01)
G06T 7/00        (2017.01)
G01N 27/447      (2006.01)
G06F 3/0484      (2013.01)
```

(52) U.S. Cl.
CPC ..... G06T 7/0012 (2013.01); G01N 27/44717 (2013.01); G01N 27/44756 (2013.01); G06T 3/40 (2013.01); *G06F 3/04842* (2013.01); *G06T 2207/20081* (2013.01); *G06T 2207/20084* (2013.01)

(58) Field of Classification Search
CPC .................................................. G06T 7/0012
See application file for complete search history.

(56) References Cited

U.S. PATENT DOCUMENTS

2009/0319450 A1* 12/2009 Teramoto ............... G16B 40/00
706/12

FOREIGN PATENT DOCUMENTS

| JP | 2003-029304 | 1/2003 |
|----|-------------|--------|
| JP | 2004-070530 | 3/2004 |
| JP | 2004-198195 | 7/2004 |

(Continued)

OTHER PUBLICATIONS

Nobuhiro Hayashi, "High accuracy and high-throughput profiling of an organism", Expected Materials for the Future, vol. 11, No. 1,Jan. 10, 2011, pp. 41-48 (Partial Translation).

*Primary Examiner* — Jitesh Patel

(74) *Attorney, Agent, or Firm* — Wenderoth, Lind & Ponack, L.L.P.

(57) ABSTRACT

A display control apparatus includes a memory and a circuit. The circuit obtains an electrophoretic image from the memory, causes a display to display the electrophoretic image as a first display image, receives a selection of a first pixel in the electrophoretic image displayed on the display, obtains one or more first useful proteins corresponding to the first pixel and one or more second useful proteins corresponding to one or more second pixels, a length between the first pixel and each of the one or more second pixels being less than or equal to a first length among the pixels, and causes the display to display the electrophoretic image, the one or more first useful proteins, and the one or more second useful proteins as a second display image.

18 Claims, 25 Drawing Sheets

(56) References Cited

FOREIGN PATENT DOCUMENTS

| | | | |
|---|---|---|---|
| JP | 2005-291759 | 10/2005 | |
| JP | 2006-162445 | 6/2006 | |
| JP | 2012-168014 | 9/2012 | |
| JP | 2013-221839 | 10/2013 | |
| WO | WO-2005091199 A2 * | 9/2005 | ......... G01N 33/6803 |
| WO | 2007/026598 | 3/2007 | |

* cited by examiner

FIG. 2

CORRESPONDENCE
                                    TABLE

| PIXEL POSITION (x,y) | y1 | y2 | y3 | y4 | y5 | y6 |
|---|---|---|---|---|---|---|
| x1 | A | A,B | B | C | C,F | F |
| x2 | A | A,B | B | C | C,F | F |
| x3 | A | B,D | B | B,C | C,F | F |
| x4 | A,D | D | B,E | E | C,F,G | F,G |
| x5 | D | D,E | E | E,G | G | G |
| x6 | D | D,E | E | E,G | G | G |

A: PROTEIN A
B: PROTEIN B
C: PROTEIN C
D: PROTEIN D
E: PROTEIN E
F: PROTEIN F
G: PROTEIN G

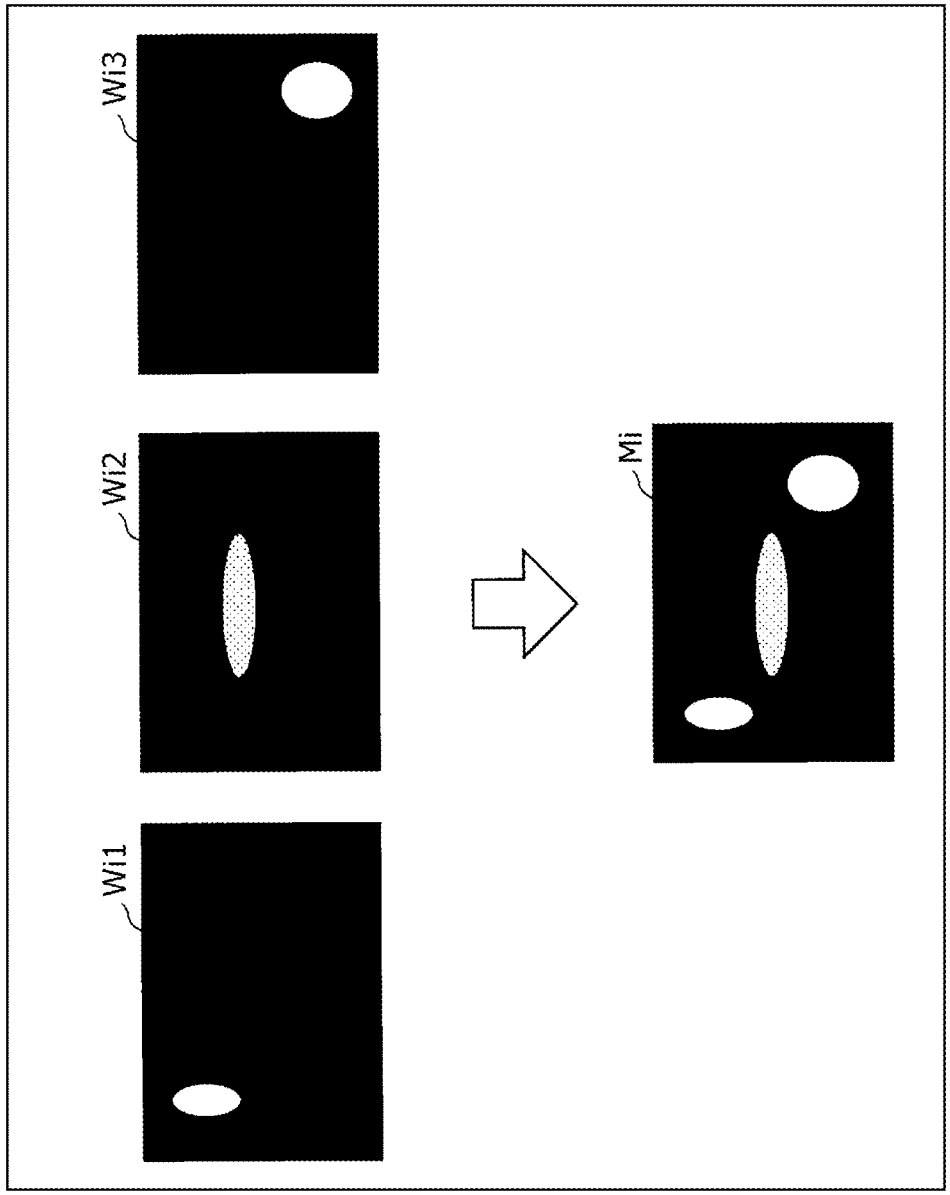

FIG. 15A
| 216 | 225 | 0 | 0 | 0 | 0 | 0 | 0 | 0 | 0 |
|---|---|---|---|---|---|---|---|---|---|
| 237 | 235 | 0 | 0 | 0 | 0 | 0 | 0 | 0 | 0 |
| 232 | 230 | 175 | 247 | 252 | 215 | 0 | 0 | 0 | 0 |
| 0 | 0 | 205 | 240 | 245 | 210 | 0 | 0 | 0 | 0 |
| 0 | 0 | 0 | 0 | 0 | 0 | 0 | 155 | 135 | 115 |
| 0 | 0 | 0 | 0 | 0 | 0 | 0 | 165 | 185 | 160 |
| 245 | 243 | 0 | 0 | 0 | 0 | 0 | 170 | 180 | 160 |
| 240 | 237 | 0 | 0 | 0 | 0 | 0 | 125 | 105 | 115 |
FIG. 15B
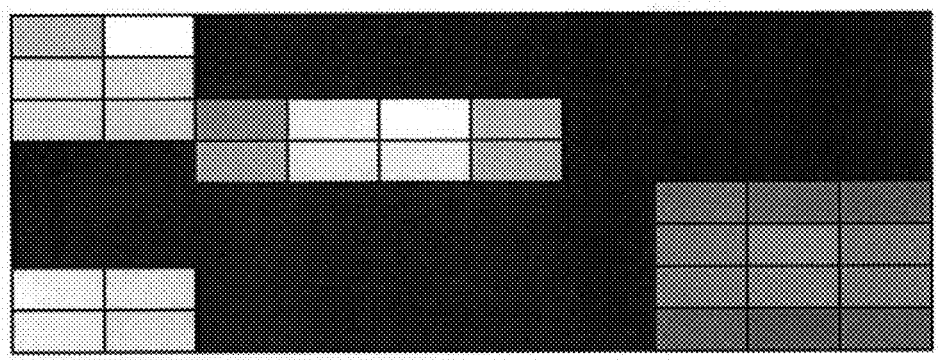
FIG. 15C
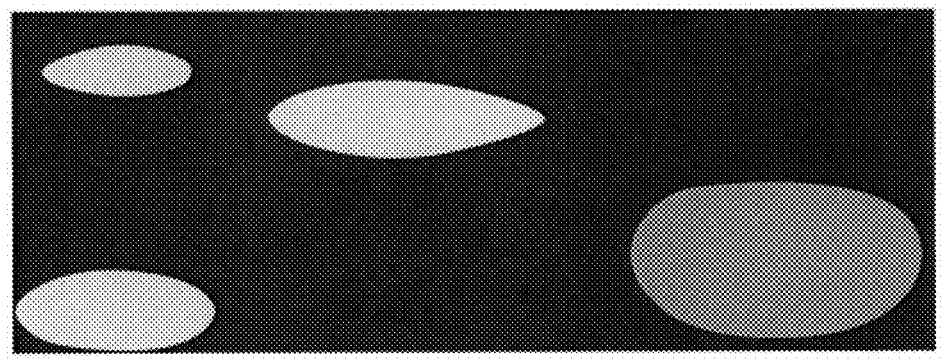

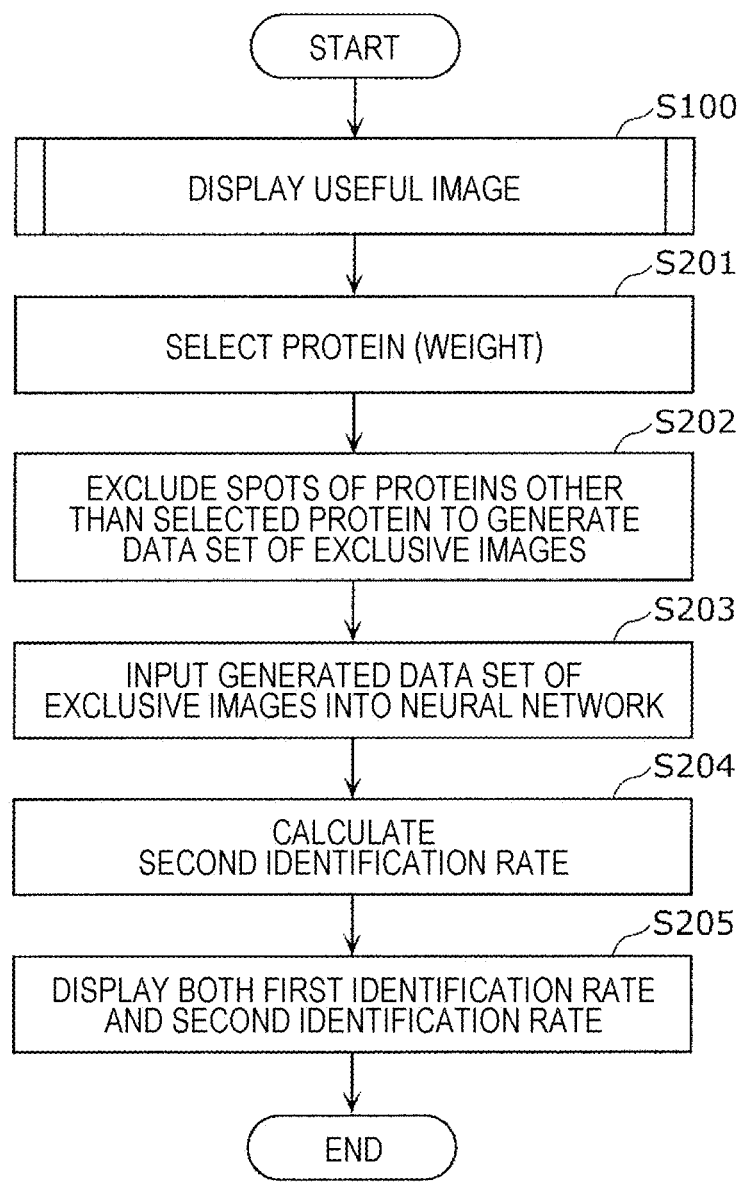

DISPLAY CONTROL APPARATUS, DISPLAY CONTROL METHOD, AND RECORDING MEDIUM

BACKGROUND

1. Technical Field

The present disclosure relates to a display control apparatus that controls display about proteins, a display control method, and a recording medium.

2. Description of the Related Art

In recent years, identification of proteins that are useful to identify diseases by using two-dimensional electrophoretic images has been extensively studied. Two-dimensional electrophoretic images are obtained by two-dimensionally separating proteins from blood and the like on the basis of the charge and molecular weight. In a display control apparatus of the related art, two two-dimensional electrophoretic images of a patient who has a disease are simultaneously displayed on a display. By using an alignment technique disclosed in Japanese Patent No. 5565842, for example, an expert visually recognizes what type of protein is appearing. Then, the expert selects a protein that is useful to identify a disease, and makes a biomarker for determining whether the selected protein is appearing. That is, the two-dimensional electrophoretic images are used to make a biomarker (for example, see Nobuhiro HAYASHI, "Bioscience, Biological Profiling with High Accuracy and High Throughput—High Performance Proteomics using Improved Two-Dimensional Electrophoretic Method for Generic Technology", Expected Materials for the Future, vol. 11, no. 1, pp. 42-49, 2011).

SUMMARY

However, in the display control apparatus of the related art, it has been difficult to know what type of protein is appearing in electrophoretic images.

One non-limiting and exemplary embodiment provides a display control apparatus and the like that enable easy understanding of one or more proteins appearing in an electrophoretic image.

In one general aspect, the techniques disclosed here feature a display control apparatus including a memory and a circuit. The memory stores an electrophoretic image including pixels and useful protein information showing relationships between the pixels and useful proteins, each of the pixels corresponding to one or more useful proteins included in the useful proteins. The circuit (a1) obtains the electrophoretic image and the useful protein information from the memory, (a2) causes a display to display the electrophoretic image as a first display image, (a3) receives a selection of a first pixel from among the pixels included in the electrophoretic image displayed on the display, (a4) obtains, on the basis of the useful protein information, (i) one or more first useful proteins that are included in the useful proteins and correspond to the first pixel and (ii) one or more second useful proteins that are included in the useful proteins and correspond to one or more second pixels, a length between the first pixel and each of the one or more second pixels being less than or equal to a first length, and (a5) causes the display to display the electrophoretic image, the one or more first useful proteins, and the one or more second useful proteins as a second display image.

It should be noted that general or specific embodiments may be implemented as a system, a method, an integrated circuit, a computer program, a computer-readable storage medium, or any selective combination thereof. Examples of the computer-readable storage medium include a non-volatile storage medium such as a compact disc-read only memory (CD-ROM).

The display control apparatus according to an embodiment enables easy understanding of one or more proteins appearing in an electrophoretic image. Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 2 illustrates an example of a correspondence table held in a memory in the first embodiment;

FIG. 14 illustrates examples of weight images and an example of a useful image in the second embodiment;

FIG. 15A illustrates a specific example of the weight image in the second embodiment;

FIG. 15B illustrates a specific example of the weight image in the second embodiment;

FIG. 15C illustrates a specific example of the weight image in the second embodiment;

FIG. 21 is a flowchart illustrating an overall processing operation of the display control apparatus according to the third embodiment;

DETAILED DESCRIPTION

Figure 1:
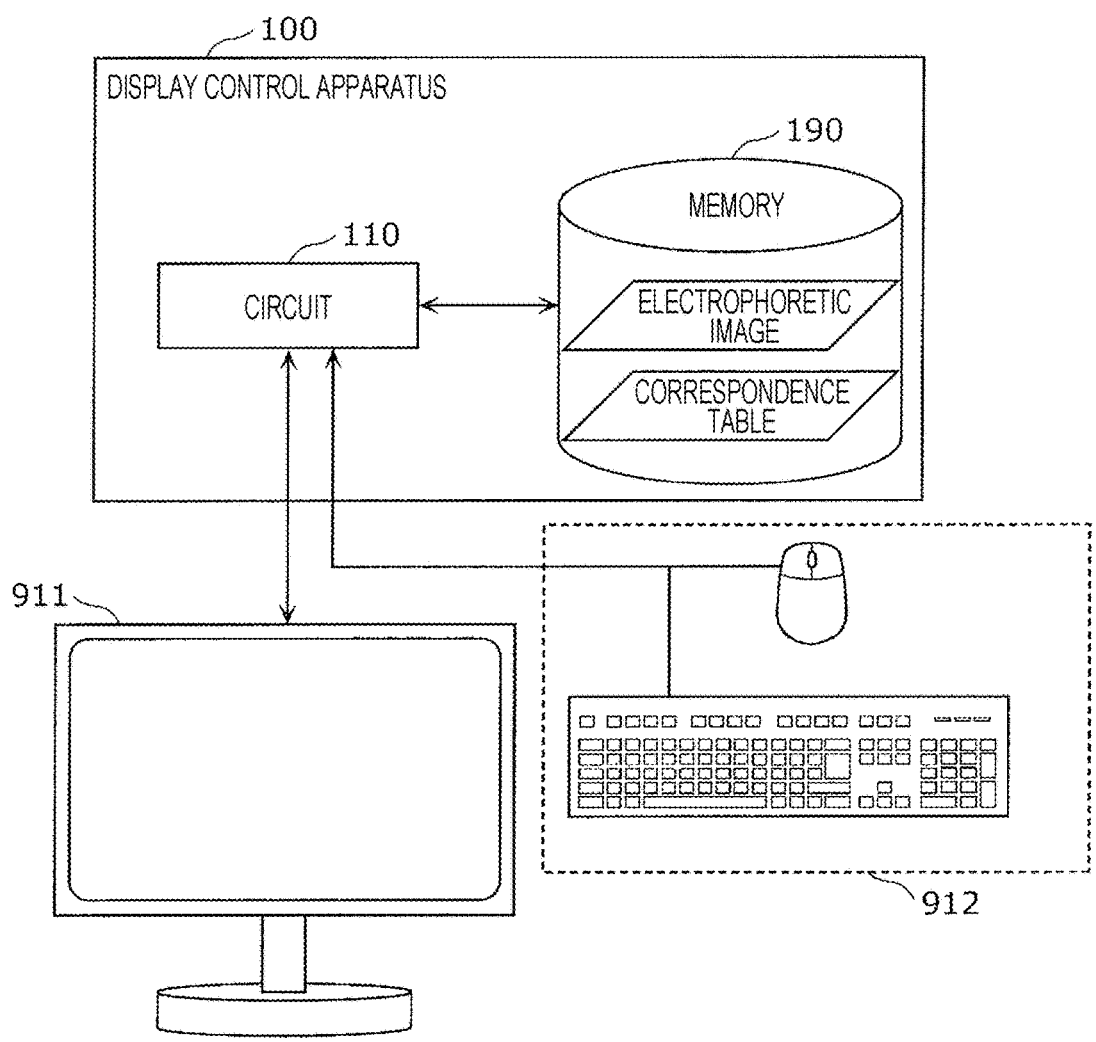
FIG. 1 is a block diagram illustrating an example of the configuration of a display control apparatus according to a first embodiment.

In order to solve the above problems, a display control apparatus according to an aspect of the present disclosure includes a memory and a circuit. The memory stores an electrophoretic image including pixels and useful protein information showing relationships between the pixels and useful proteins, each of the pixels corresponding to one or more useful proteins included in the useful proteins. The circuit (a1) obtains the electrophoretic image and the useful protein information from the memory, (a2) causes a display to display the electrophoretic image as a first display image, (a3) receives a selection of a first pixel from among the pixels included in the electrophoretic image displayed on the display, (a4) obtains, on the basis of the useful protein information, (i) one or more first useful proteins that are included in the useful proteins and correspond to the first pixel and (ii) one or more second useful proteins that are included in the useful proteins and correspond to one or more second pixels, a length between the first pixel and each of the one or more second pixels being less than or equal to a first length, and (a5) causes the display to display the electrophoretic image, the one or more first useful proteins, and the one or more second useful proteins as a second display image.

Thus, by selecting the first pixel, a user can easily understand, not only the one or more first useful proteins appearing and corresponding to the first pixel in the electrophoretic image, but also the one or more second useful proteins appearing and corresponding to the one or more second pixels near the first pixel.

For example, if the one or more first useful proteins include a third useful protein and a fourth useful protein in the (a4), the circuit may cause one or more third pixels and one or more fourth pixels to be displayed in an emphasized manner in the electrophoretic image in the second display image, the one or more third pixels corresponding to the third useful protein, the one or more fourth pixels corresponding to the fourth useful protein.

Thus, by the user selecting the first pixel, the one or more third pixels and the one or more fourth pixels are displayed in an emphasized manner. Accordingly, by selecting the first pixel, the user can easily understand the third useful protein and the fourth useful protein that are appearing and corresponding to the first pixel in the electrophoretic image.

In addition, the circuit may (a6) receive a selection of any of the one or more first useful proteins or the one or more second useful proteins while the second display image is displayed, and may (a7) cause the display to display one or more fifth pixels in an emphasized manner in the electrophoretic image in the second display image, the one or more fifth pixels corresponding to the useful protein whose selection has been received.

Thus, by selecting the useful protein, the user can easily understand the one or more fifth pixels corresponding to the useful protein in the electrophoretic image.

In addition, between the (a2) and the (a3), the circuit may (a8) receive an enlarge operation of the electrophoretic image or a reduce operation of the electrophoretic image centering one or more pixels among the pixels in the first display image, and may, (a9) on the basis of the received enlarge operation or the received reduce operation, changes a magnifying power of the electrophoretic image in the first display image and causes the display to display the electrophoretic image with the changed magnifying power. After the selection of the first pixel has been received in the (a3), at least in the (a4) or the (a5), the magnifying power of the electrophoretic image is not necessarily changed in accordance with the enlarge operation or the reduce operation.

Thus, by enlarging or reducing the electrophoretic image, the first pixel can easily be selected. In addition, since the magnifying power is not changed in the electrophoretic image after the selection, it is possible to prevent pixels corresponding to the one or more first useful proteins and the one or more second useful proteins from becoming hard to see as a result of change in the magnifying power.

A display control apparatus according to another aspect of the present disclosure includes a memory and a circuit. The memory includes a data set formed of electrophoretic images. The circuit (b1) learns a relationship between the electrophoretic images and a disease by using the data set and a neural network, (b2) images weights in the neural network obtained from a result of the learning of the relationship to generate a weight image group formed of one or more weight images, (b3) calculates a disease identification rate of the data set in the neural network as a first identification rate, (b4) generates a useful image by using the weight image group, and (b5) causes a display to display both the useful image and the first identification rate. The useful image includes pixels. The pixels include a pixel i having a pixel value i and corresponding to a useful protein i, a pixel j having a pixel value j and corresponding to a useful protein j, and a pixel k having a pixel value k and corresponding to a useful protein k. If the useful protein i is most useful to identify the disease and the useful protein k is least useful to identify the disease among the useful protein i, the useful protein j, and the useful protein k, the pixel value i>the pixel value j>the pixel value k is set, or the pixel value i<the pixel value j<the pixel value k is set.

Thus, since the useful image and the first identification rate are displayed, it is possible to easily understand a protein that is appearing obviously in the electrophoretic image of a person who has the disease.

That is, since a display control apparatus of the related art does not use statistic information, it is not possible to sweep away differences unique to individual patients. In addition, it is not possible to quantify the accuracy of detecting a disease by using a specific protein. Accordingly, it remains unknown whether the protein is useful to identify a disease unless a biomarker using the protein is made. However, a display control apparatus according to an aspect of the present disclosure generates a useful image in which a pixel corresponding to a protein that is useful to identify a disease has a small or large pixel value by using the weights obtained from the result of the learning of the neural network. In addition, the effectiveness of the protein is displayed as the first identification rate. Therefore, it is possible to present the protein that is statistically useful to identify a disease regardless of the differences between individual patients without making a biomarker.

For example, in the (b4), the useful image may be generated by averaging pixel values of pixels at identical positions in the one or more weight images included in the weight image group.

Thus, it is possible to easily generate the useful image from the weight images.

In addition, the circuit may further (b6) make a list of information of proteins corresponding to one or more spots appearing in the useful image to generate a useful protein list and may further cause, in the (b5), the display to display the useful protein list together with the useful image.

Thus, the user can easily know the information of proteins corresponding to one or more spots appearing in the useful image by seeing the useful protein list without additionally searching for the information.

In addition, the circuit may further (b7) select, in response to a selection of any one spot from among the one or more spots appearing in the useful image, or a selection of any one piece of information from the useful protein list, a single protein corresponding to the selected spot or the selected piece of information as a selected protein.

Furthermore, the circuit may further (b8) set one or more weights not corresponding to the selected protein among the weights in the neural network to zero to change the neural network, (b9) input the electrophoretic images included in the data set into the changed neural network to calculate an identification rate of the data set in the changed neural network as a second identification rate, and (b10) cause the display to display the second identification rate.

Thus, the user can easily know the disease identification rate as the second identification rate by using the selected protein.

In addition, the circuit may further (b11) exclude, from the respective electrophoretic images included in the data set, spots not corresponding to the selected protein to generate exclusive images, (b12) input the exclusive images into the neural network to calculate an identification rate of the exclusive images in the neural network as a second identification rate, and (b13) cause the display to display the second identification rate.

Thus, it is possible to calculate the second identification rate without changing the neural network.

Furthermore, the circuit may further (b14) determine, for each of non-selected proteins, which are proteins other than the selected protein, the number of weight images including a spot of the selected protein and spots of the non-selected proteins from the weight image group, (b15) extract, in a descending order of the number of weight images, from the non-selected proteins, N, which is an integer greater than or equal to 1, non-selected proteins from a first non-selected protein to an N-th non-selected protein, and (b16) cause the display to display information of each of the extracted N non-selected proteins.

Thus, the user can easily know the N non-selected proteins (i.e., combination proteins) by which the identification rate is increased by being combined with the selected protein.

It should be noted that general or specific embodiments may be implemented as a system, a method, an integrated circuit, a computer program, a computer-readable storage medium such as a CD-ROM, or any selective combination thereof.

Now, the embodiments will specifically be described with reference to the drawings.

Note that each of the following embodiments will illustrate general or specific examples. The numeric values, shapes, materials, components, the arrangement and connection of the components, steps, the order of the steps, and the like illustrated in the following embodiments are examples and shall not limit the present disclosure. In addition, the components in the following embodiments are optional unless described in an independent claim representing the most superordinate concept.

Each of the drawings is a schematic drawing and is not strictly illustrated. In addition, the same members are denoted by the same reference numerals in the drawings.

First Embodiment

Overall Configuration

FIG. 1 is a block diagram illustrating an example of the configuration of a display control apparatus according to this embodiment.

A display control apparatus 100 according to this embodiment controls display of a display 911 and includes a memory 190 and a circuit 110.

The memory 190 is formed of, for example, a read only memory (ROM), a random access memory (RAM), or the like. The memory 190 stores an electrophoretic image including pixels and information of one or more useful proteins to which each of the pixels corresponds. The electrophoretic image herein is the above-described two-dimensional electrophoretic image. In addition, the useful proteins are proteins that are useful to identify a disease, by which a disease can be correctly identified at a rate of, for example, 70%. Such useful proteins are usable as biomarkers.

The information of the above-described one or more useful proteins indicates, for example, the names, features, properties, or the like of the useful proteins and corresponds to the position of the corresponding pixel in the electrophoretic image. That is, the memory 190 holds a correspondence table that illustrates the information of the one or more useful proteins to which each of the pixels corresponds in the electrophoretic image.

FIG. 2 illustrates an example of the correspondence table held in the memory 190.

For example, a pixel at a position (x1, y1) in the electrophoretic image corresponds to Protein A. In addition, a pixel at a position (x1, y2) in the electrophoretic image corresponds to Protein A and Protein B. Note that Protein A to Protein G each represent, for example, the type or name of protein. In this manner, the correspondence table illustrates information such as the name or the like of the one or more useful proteins to which each of the pixels corresponds in the electrophoretic image.

The circuit 110 is formed of, for example, a central processing unit (CPU), a processor, or the like. The circuit 110 controls display of the display 911 by using the memory 190 in accordance with operation on an input device 912 formed of a keyboard, a mouse, or the like.

Image Display Example

The circuit 110 in this embodiment first obtains the electrophoretic image and the correspondence table from the memory 190. The circuit 110 causes the display 911 to display the electrophoretic image as a first display image.

Figure 3A:
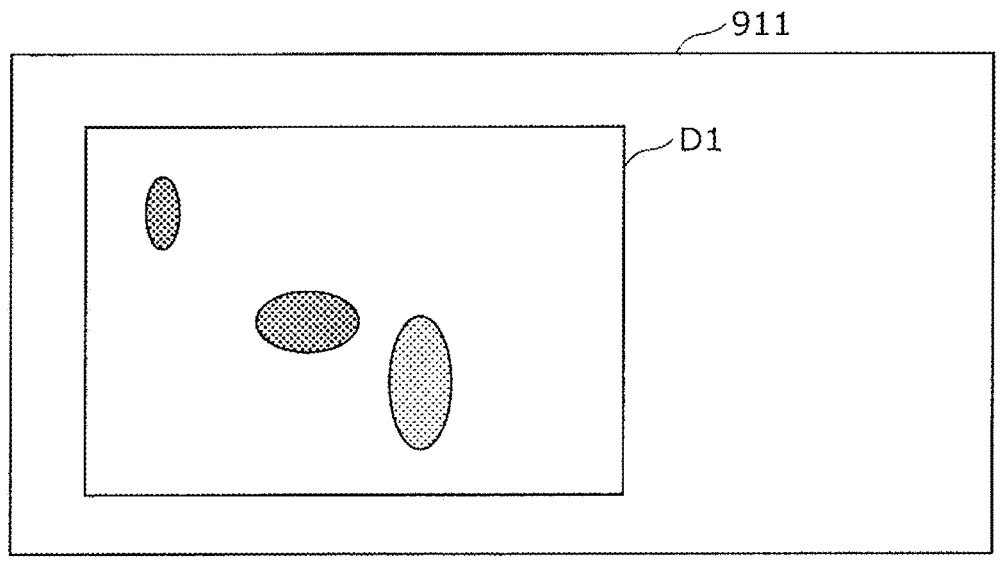
FIG. 3A illustrates an example of a first display image in the first embodiment.

FIG. 3A illustrates an example of the first display image.

The circuit 110 causes the display 911 to display the electrophoretic image as a first display image D1.

Then, the circuit 110 receives a selection of a first pixel in the electrophoretic image displayed on the display 911.

Figure 3B:
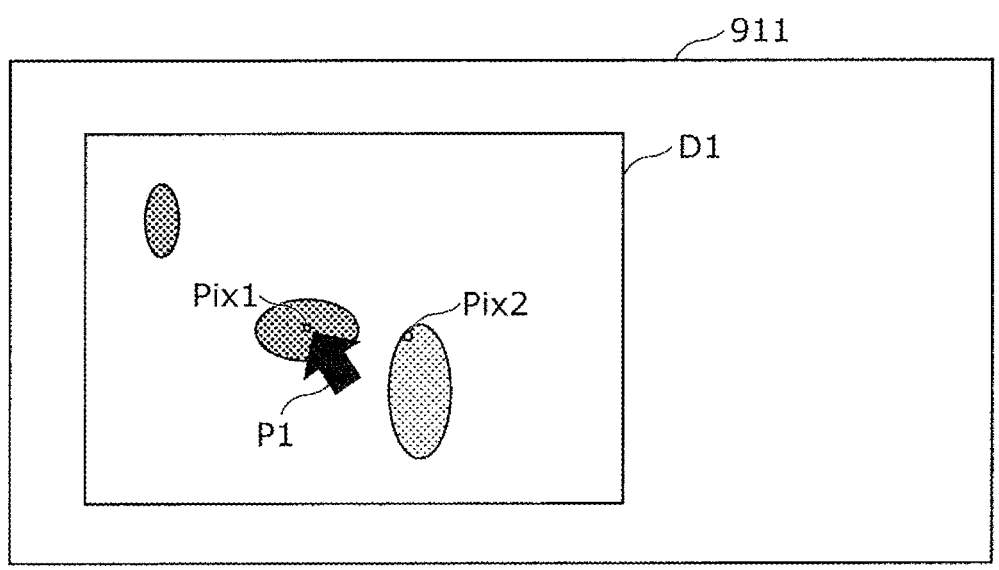
FIG. 3B illustrates an example of a selection of a first pixel in the first embodiment.

FIG. 3B illustrates an example of a selection of the first pixel.

In accordance with a movement signal from the input device 912 operated by a user, the circuit 110 moves a pointer P1 displayed on the display 911. In accordance with a selection signal from the input device 912 operated by the user, the circuit 110 receives a selection of a first pixel Pix1 indicated by the pointer P1.

Then, in accordance with the correspondence table, the circuit 110 obtains one or more first useful proteins corresponding to the first pixel Pix1 and one or more second useful proteins corresponding to one or more second pixels Pix2, the length between the first pixel Pix1 and each of the one or more second pixels Pix2 being less than or equal to a first length among the pixels. Then, the circuit 110 causes the display 911 to display the one or more first useful proteins, the one or more second useful proteins, and the electrophoretic image as a second display image. The first length is, for example, 10 to 20% length of the width or height of the electrophoretic image.

Figure 4:
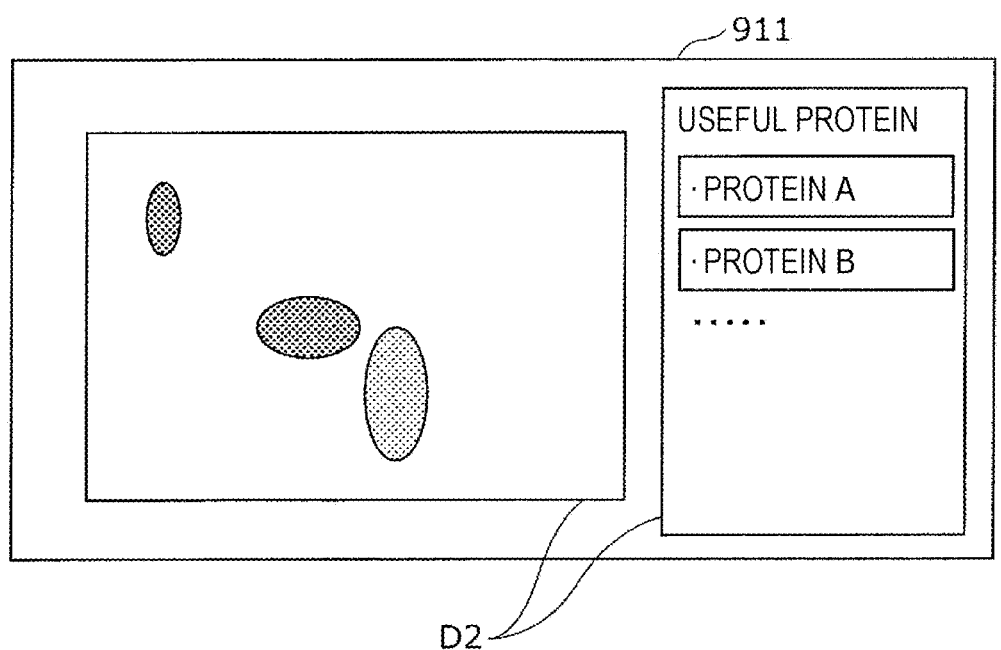
FIG. 4 illustrates an example of a second display image in the first embodiment.

FIG. 4 illustrates an example of the second display image.

When causing the display 911 to display a second display image D2, for example, the circuit 110 makes a list of "Protein A", which is the name of one of the first useful proteins, and "Protein B", which is the name of one of the second useful proteins, and causes the list to be displayed.

Thus, by selecting the first pixel Pix1, the user can easily understand, not only the one of the first useful proteins appearing and corresponding to the first pixel Pix1 in the electrophoretic image, but also the second useful protein appearing and corresponding to the second pixel Pix2 near the first pixel Pix1.

In addition, if the one or more first useful proteins include a third useful protein and a fourth useful protein, the circuit 110 causes one or more third pixels and one or more fourth pixels to be displayed in an emphasized manner in the electrophoretic image in the second display image D2, the one or more third pixels corresponding to the third useful protein, and the one or more fourth pixels corresponding to the fourth useful protein.

Figure 5:
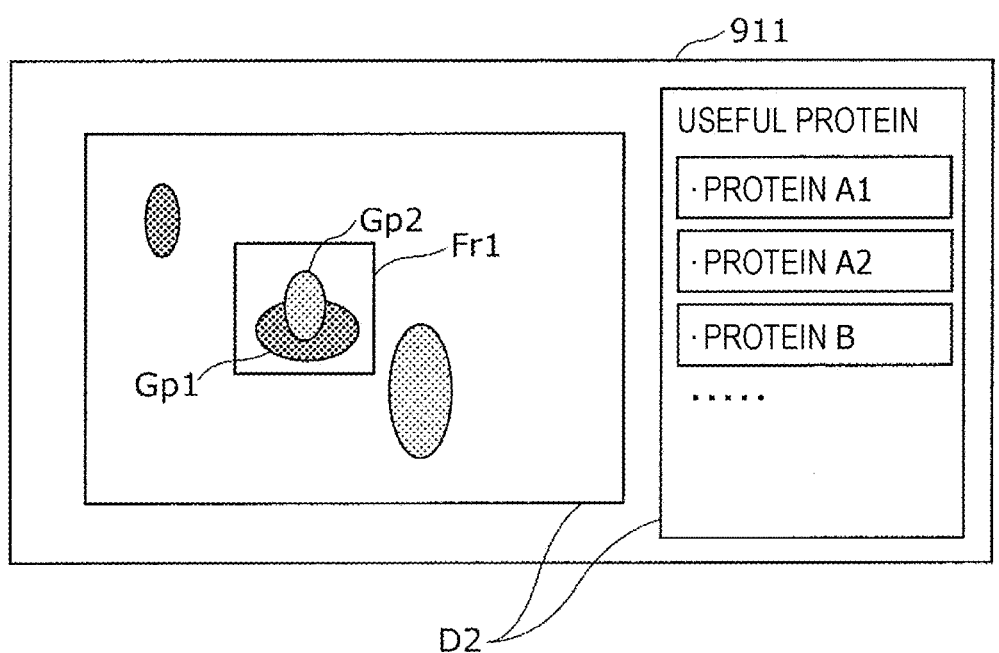
FIG. 5 illustrates another example of the second display image in the first embodiment.

FIG. 5 illustrates another example of the second display image D2.

For example, in the correspondence table, proteins named "Protein A1" and "Protein A2" correspond to the first pixel as the first useful proteins. In such a case, the one or more first useful proteins include the third useful protein named "Protein A1" and the fourth useful protein named "Protein A2".

In this case, as illustrated in FIG. 5, the circuit 110 causes a pixel group Gp1 and a pixel group Gp2 to be displayed in an emphasized manner in the electrophoretic image in the second display image D2. The pixel group Gp1 is formed of one or more third pixels corresponding to the third protein "Protein A1", and the pixel group Gp2 is formed of one or more fourth pixels corresponding to the fourth protein "Protein A2". For example, the circuit 110 emphasizes the pixel group Gp1 and the pixel group Gp2 by causing a frame Fr1 surrounding the pixel group Gp1 and the pixel group Gp2 to be displayed. Note that the method for emphasizing the pixel group Gp1 and the pixel group Gp2 is not limited to the example illustrated in FIG. 5, and the color of the pixel groups may be changed, a line along the periphery of the pixel groups may be displayed, or the pixel groups may be blinked.

Thus, by the user selecting the first pixel Pix1, the pixel group Gp1 and the pixel group Gp2 are displayed in an emphasized manner. Accordingly, by selecting the first pixel Pix1, the user can easily understand the third useful protein "Protein A1" and the fourth useful protein "Protein A2" appearing and corresponding to the first pixel Pix1 in the electrophoretic image.

In addition, while the second display image D2 is displayed, the circuit 110 may receive a selection of any of the one or more first useful proteins or the one or more second useful proteins. In this case, the circuit 110 causes the display 911 to display, in the electrophoretic image in the second display image D2, one or more fifth pixels corresponding to the useful protein whose selection has been received.

Figure 6:
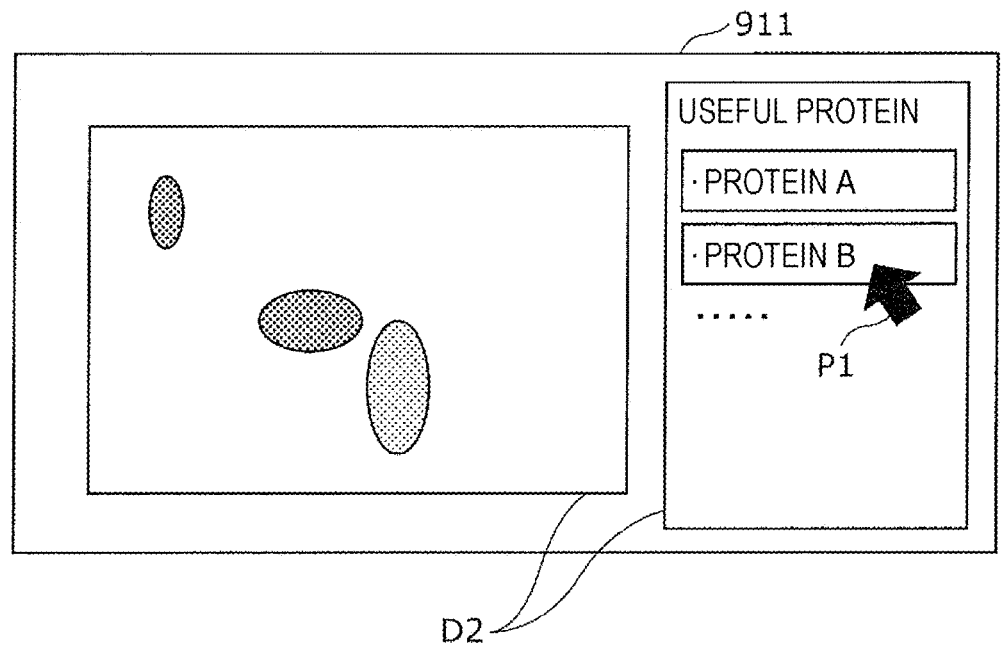
FIG. 6 illustrates an example of a selection of a second useful protein in the first embodiment.
Figure 7:
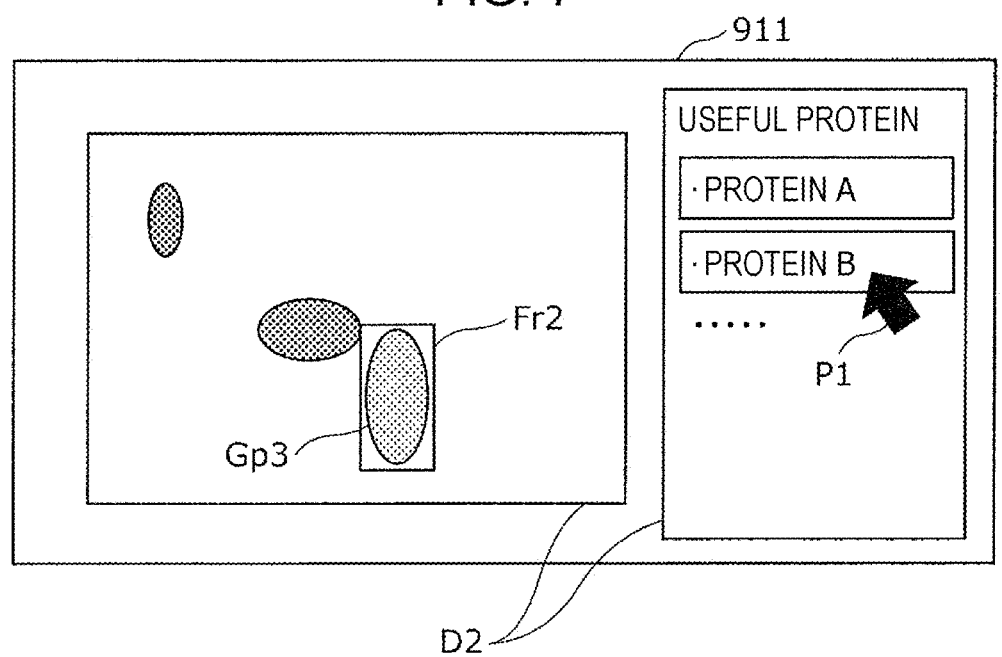
FIG. 7 illustrates an example in which one or more fifth pixels are emphasized in the first embodiment.

FIG. 6 illustrates an example of a selection of a second useful protein. FIG. 7 illustrates an example in which the one or more fifth pixels are emphasized.

As illustrated in FIG. 6, in accordance with a movement signal from the input device 912 operated by the user, the circuit 110 moves the pointer P1 displayed on the display 911. Then, in accordance with a selection signal from the input device 912, the circuit 110 receives the name of the second useful protein indicated by the pointer P1. For example, the circuit 110 receives the name "Protein B" of the second useful protein.

Then, as illustrated in FIG. 7, the circuit 110 causes the display 911 to display a pixel group Gp3 in an emphasized manner in the electrophoretic image in the second display image D2. The pixel group Gp3 is formed of the one or more fifth pixels corresponding to the useful protein "Protein B" whose selection has been received. For example, the circuit 110 emphasizes the pixel group Gp3 by displaying a frame Fr2 surrounding the pixel group Gp3. Note that the method for emphasizing the pixel group Gp3 is not limited to the example illustrated in FIG. 7, and the color of the pixel group Gp3 may be changed, a line along the periphery of the pixel group Gp3 may be displayed, or the pixel group Gp3 may be blinked.

Thus, by selecting a useful protein, the user can easily understand the pixel group corresponding to the useful protein in the electrophoretic image.

In addition, the circuit 110 may receive an enlarge operation or a reduce operation after display of the first display image D1 illustrated in FIG. 3A before reception of the selection of the first pixel illustrated in FIG. 3B. The enlarge operation is an operation for enlarging the electrophoretic image centering one or more pixels among the pixels in the first display image D1. The reduce operation is an operation for reducing the electrophoretic image. In this case, in accordance with the received enlarge or reduce operation, the circuit 110 changes the magnifying power of the electrophoretic image in the first display image D1, and causes the display 911 to display the electrophoretic image with the changed magnifying power. Then, after the selection of the first pixel has been received, the circuit 110 does not change the magnifying power of the electrophoretic image in accordance with the enlarge or reduce operation at least while the one or more first useful proteins and the one or more second useful proteins are obtained and while the second display image D2 is displayed.

Thus, by enlarging or reducing the electrophoretic image, the first pixel Pix1 can be easily selected. In addition, since the magnifying power of the electrophoretic image is not changed after the selection, it is possible to prevent pixels corresponding to the one or more first useful proteins and the one or more second useful proteins from becoming hard to see as a result of change in the magnifying power.

Figure 8:
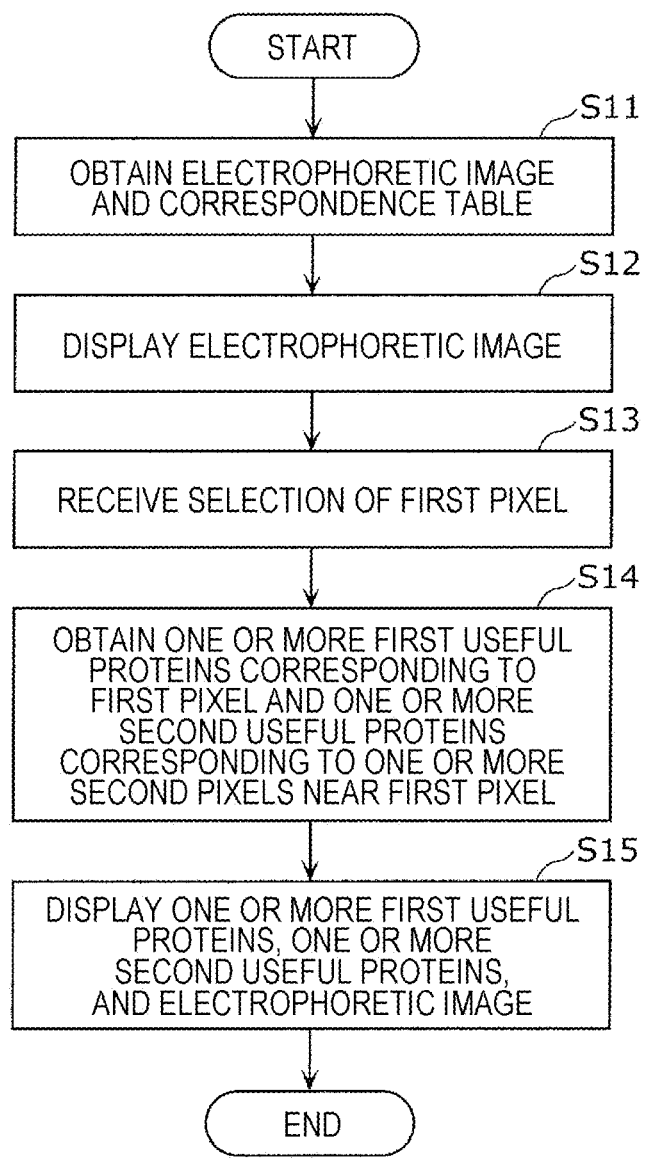
FIG. 8 is a flowchart illustrating an outline of a processing operation of a circuit in the first embodiment.

FIG. 8 is a flowchart illustrating an outline of a processing operation of the circuit 110 in this embodiment.

[Step S11]

First, the circuit 110 of the display control apparatus 100 obtains the electrophoretic image and the correspondence table including information of the one or more useful proteins from the memory 190.

[Step S12]

Subsequently, the circuit 110 causes the display 911 to display the electrophoretic image as the first display image D1.

[Step S13]

Subsequently, the circuit 110 receives a selection of the first pixel in the electrophoretic image displayed on the display 911.

[Step S14]

Subsequently, on the basis of the correspondence table including information of the one or more useful proteins, the circuit 110 obtains the one or more first useful proteins corresponding to the first pixel and the one or more second useful proteins corresponding to one or more second pixels, the length between the first pixel and each of the one or more second pixels being less than or equal to a first length among the pixels.

[Step S15]

Subsequently, the circuit 110 causes the display 911 to display the one or more first useful proteins, the one or more second useful proteins, and the electrophoretic image as the second display image D2.

Such a display control apparatus 100 according to this embodiment enables easy understanding of proteins appearing in the electrophoretic image.

Second Embodiment

A display control apparatus according to this embodiment has the same functions as the display control apparatus 100 according to the first embodiment and also converts the electrophoretic image obtained from blood or the like into a useful image. In the useful image, a pixel corresponding to a protein that is useful to identify a disease has a larger pixel value than a pixel corresponding to a protein that is not useful to identify the disease. Alternatively, in the useful image, a pixel corresponding to a protein that is useful to identify the disease has a smaller pixel value than a pixel corresponding to a protein that is not useful to identify the disease.

The electrophoretic image in the first embodiment corresponds to a useful image in this embodiment. That is, by using a data set formed of electrophoretic images and a neural network, the display control apparatus according to this embodiment learns a relationship between the electrophoretic images and a disease to generate a useful image in accordance with the weights in the neural network. In addition, the display control apparatus according to this embodiment calculates a disease identification rate of the data set in the neural network and causes the display 911 to display the identification rate and the useful image.

Overall Configuration

Figure 9:
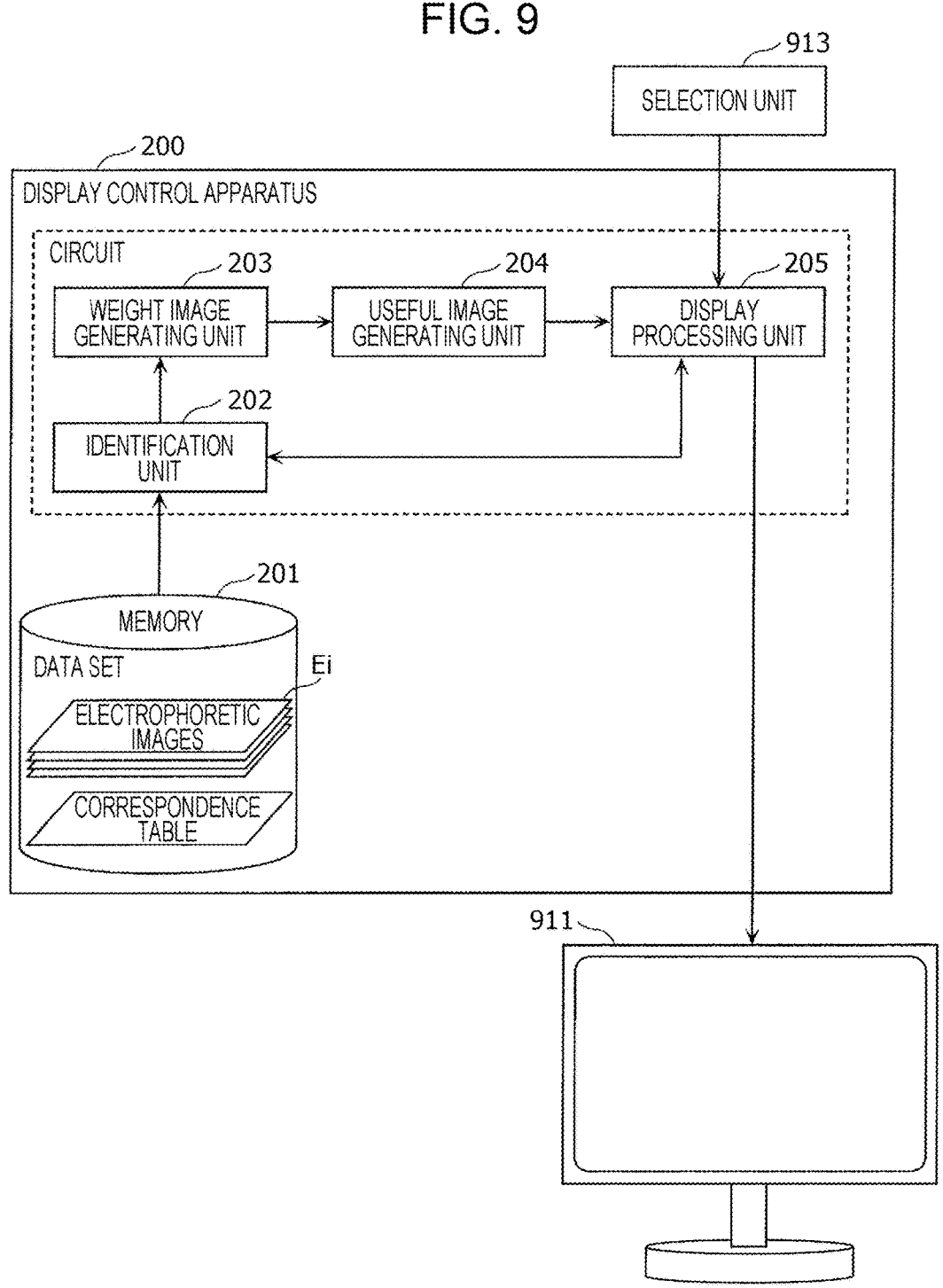
FIG. 9 is a block diagram illustrating an example of a functional configuration of a display control apparatus according to a second embodiment.

FIG. 9 is a block diagram illustrating an example of a functional configuration of the display control apparatus according to this embodiment. As illustrated in FIG. 9, a display control apparatus 200 according to this embodiment includes a memory 201, an identification unit 202, a weight image generating unit 203, a useful image generating unit 204, and a display processing unit 205. In accordance with the operation of a selection unit 913 that corresponds to the input device 912 in the first embodiment, such a display control apparatus 200 controls display of the display 911.

Note that the components of the display control apparatus 200 other than the memory 201 may be, for example, realized as a software function enabled by an image processor or a microprocessor executing a predetermined program. In addition, the identification unit 202, the weight image generating unit 203, the useful image generating unit 204, and the display processing unit 205 may be configured from one or more circuits.

The memory 201 stores the above-described correspondence table and a data set formed of electrophoretic images Ei. Specifically, the memory 201 stores, as a data set, one or more electrophoretic images Ei of one or more persons who have a predetermined disease and one or more electrophoretic images Ei of one or more persons who do not have the predetermined disease.

Figure 10:
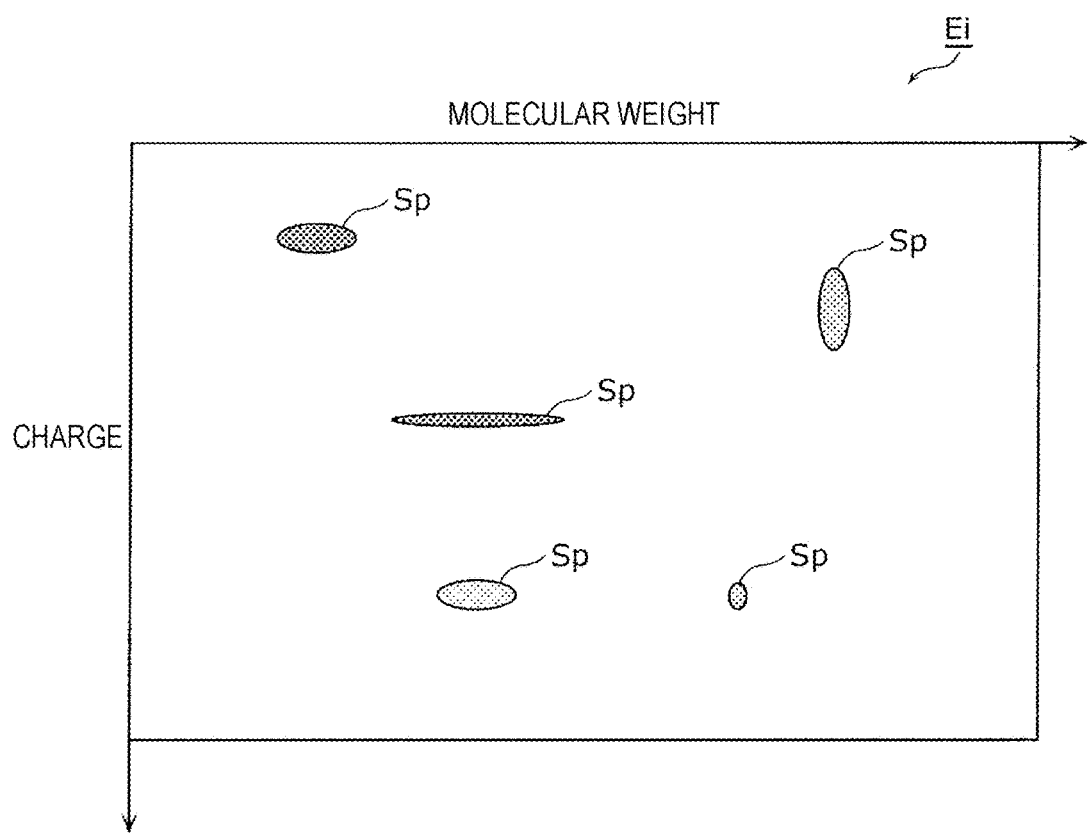
FIG. 10 illustrates a schematic diagram of an electrophoretic image in the second embodiment.

FIG. 10 illustrates a schematic diagram of an electrophoretic image Ei.

The electrophoretic image Ei is the above-described two-dimensional electrophoretic image and is obtained by two-dimensionally separating proteins obtained from a blood sample or the like of a person (e.g., patient) on the basis of the charge and molecular weight. From such an electrophoretic image Ei, the patient's status can be obtained on the basis of the position or concentration (i.e., pixel value) of fluorescent regions or staining regions (hereinafter referred to as spots) Sp corresponding to the respective separated proteins. That is, in the electrophoretic image Ei of each patient, a protein corresponding to a pixel at a specific position is common to all patients, and when the pixel is specified, the protein corresponding to the pixel is uniquely determined. The correspondence table stored in the memory 201 illustrates correspondence between each pixel and each protein as in the first embodiment. In addition, the disease is, for example, sepsis. Sepsis is a type of systemic inflammatory response syndrome and needs to be detected early in the medical field. Although this embodiment will be described by taking sepsis as the disease, the disease may be any illness other than sepsis.

The identification unit 202 includes a neural network and learns a relationship between the electrophoretic images Ei and the disease by using the data set and the neural network. In addition, the identification unit 202 calculates a disease identification rate of the data set in the neural network as a first identification rate. This identification rate is, for example, an accuracy rate of identifying sepsis or non-sepsis for each electrophoretic image Ei included in the data set.

The weight image generating unit 203 images weights in the neural network obtained from a result of the learning of the above-described relationship to generate a weight image group formed of one or more weight images.

The useful image generating unit 204 generates a useful image by using the weight image group. The useful image is formed of pixels each corresponding to one or more proteins. A pixel corresponding to a protein that is useful to identify a disease has a smaller or larger pixel value than a pixel corresponding to a protein that is not useful to identify the disease.

The display processing unit 205 causes the display 911 to display both the useful image and the first identification rate. That is, the display processing unit 205 obtains the useful image from the useful image generating unit 204 and obtains the first identification rate from the identification unit 202 to cause the display 911 to display the useful image and the first identification rate.

The selection unit 913 corresponds to the input device 912 in the first embodiment and changes display of the display 911 by outputting a signal in accordance with a user operation to the display processing unit 205.

Learning of Identification Unit

As described above, the identification unit 202 performs learning based on the neural network.

Figure 11:
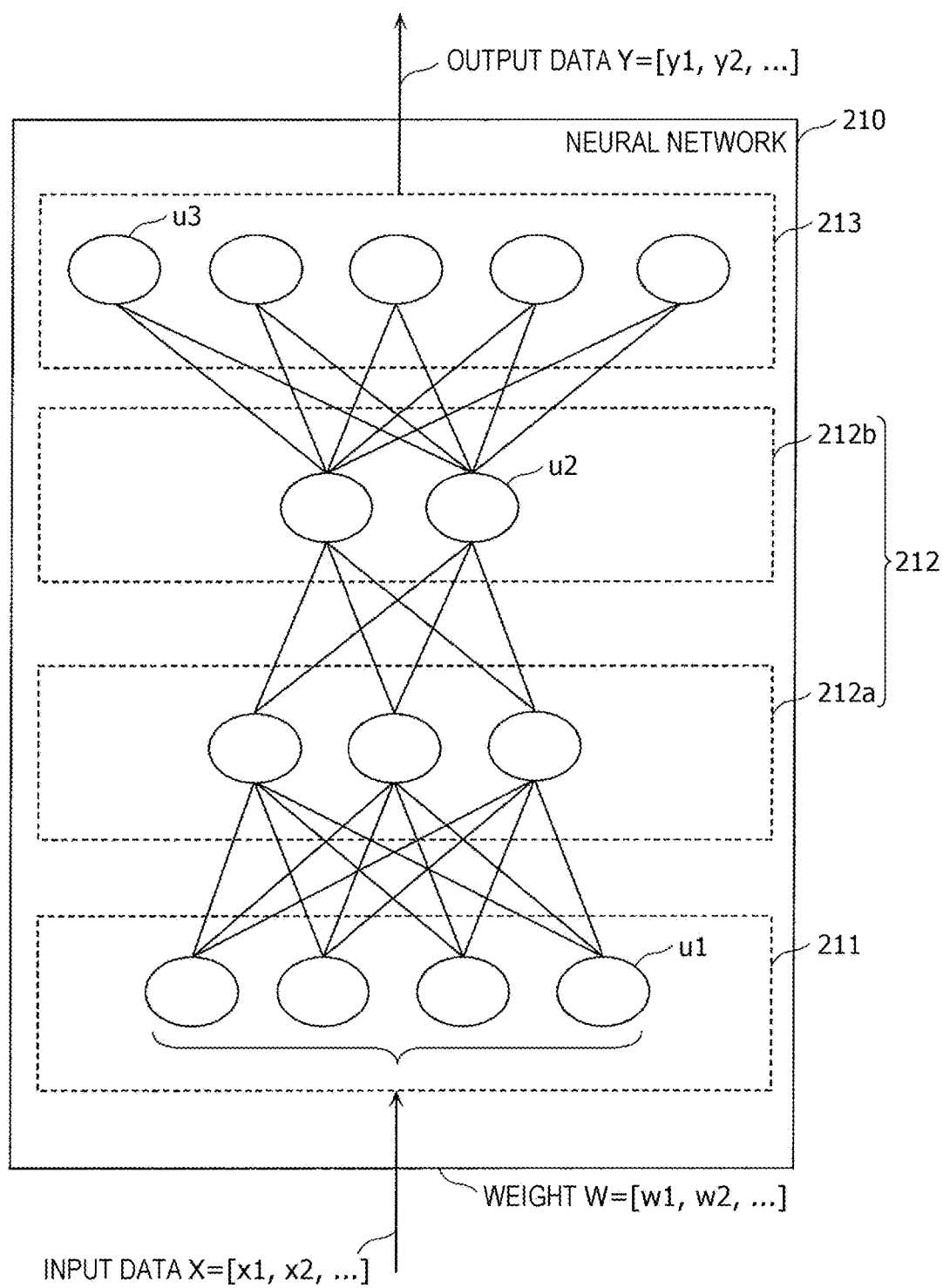
FIG. 11 is a conceptual diagram for illustrating a calculation model of the neural network in the second embodiment.

FIG. 11 is a conceptual diagram for illustrating a computation model of the neural network. The neural network is, as is commonly known, a computation apparatus that performs computation in accordance with a computation model simulating a biological neural network.

As illustrated in FIG. 11, a neural network 210 includes units (white circles illustrated in FIG. 11) corresponding to neurons. Each of the units is disposed in any of an input layer 211, a hidden layer 212, and an output layer 213.

Although the hidden layer 212 in the example illustrated in FIG. 11 is formed of two layers, which are a hidden layer 212a and a hidden layer 212b, the hidden layer 212 may be formed of a single hidden layer or three or more hidden layers. Note that the neural network including hidden layers is particularly called a multi-layer neural network apparatus in some cases.

Now, among the layers included in the neural network 210, layers close to the input layer 211 are referred to as lower layers, and layers close to the output layer 213 are referred to as upper layers. Each unit in the neural network 210 is a computational element that combines computation results received from the units disposed in a lower layer in accordance with a weight (e.g., weighted sum computation or weighted addition) and transmits the result of combination to a unit disposed in an upper layer.

Functions of the neural network 210 are defined by configuration information indicating the number of layers included in the neural network 210 and the number of units disposed in each layer and by a weight W=[w1, w2, ... ] used by each unit for the weighted sum computation.

As illustrated in FIG. 11, values of elements included in input data X=[x1, x2, ... ] are input into each unit u1 in the input layer 211 in the neural network 210. For example, if the input data X is the electrophoretic image Ei, the pixel value of the electrophoretic image Ei is input into each unit u1 in the input layer 211. That is, if the electrophoretic image Ei is formed of 1500×1500 pixels, the input layer 211 includes 1500×1500 units u1. Then, the pixel value of a pixel corresponding to a unit u1 is input into each unit u1.

Thus, in each unit u2 in the hidden layer 212 and each unit u3 in the output layer 213, weighted sum computation using the weight W=[w1, w2, ... ] is performed. As a result, output data Y=[y1, y2, ... ] is output from the output layer 213. Each element of the output data Y=[y1, y2, ... ] is a value indicating the result of weighted sum computation performed by the units u3 in the output layer 213.

Such a neural network 210 solves a classification problem for classifying the input data X. More specifically, in the neural network 210, the units u3 in the output layer 213 correspond to correct labels that are different from one another for classifying the input data X. The weight W is adjusted such that, when the elements of the input data X are input, the output value of each unit u3 in the output layer 213 corresponding to the correct label of the input data X approaches 1 and the output values of the other units u3 approach 0.

Figure 12:
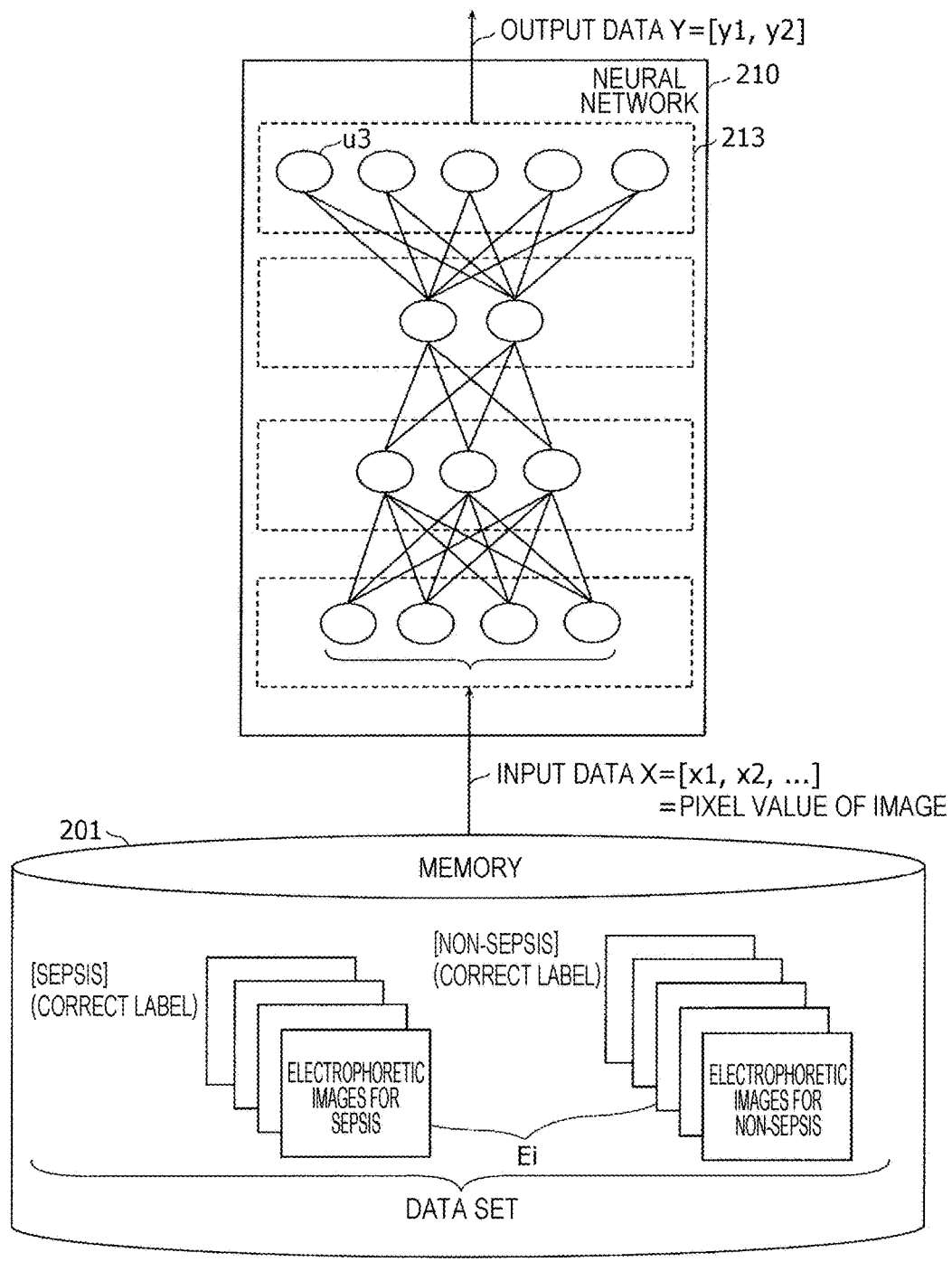
FIG. 12 illustrates a learning example in which correct labels are "sepsis" and "non-sepsis" in the second embodiment.

FIG. 12 illustrates a learning example in which correct labels are "sepsis" and "non-sepsis".

As illustrated in FIG. 12, in the neural network 210, each of the units u3 in the output layer 213 corresponds to a correct label of either one of a correct label "sepsis" and a correct label "non-sepsis". In addition, the weight W is adjusted such that the output data Y=[1, 0] is obtained for an electrophoretic image Ei serving as learning data with the correct label "sepsis" and that output data Y=[0, 1] is obtained for an electrophoretic image Ei serving as learning data with the correct label "non-sepsis".

Note that in a case of performing supervised learning in the neural network 210, for example, by using the input data X, the weight W, and the correct labels, a loss function representing an error between either of the correct labels and the output data Y may be defined, and the weight W may be updated in accordance with a gradient for decreasing the loss function based on gradient descent.

In addition, in a case in which the neural network 210 is a multi-layer neural network apparatus, in particular, before the above-described supervised learning, unsupervised learning called layer-wise pre-training may be performed to adjust the weight W individually in each hidden layer. With this configuration, the weight W that enables more accurate classification is obtained through supervised learning performed later.

In addition, for adjusting the weight W in the neural network 210, in addition to the above-described gradient descent, for example, a known algorithm such as backpropagation may be used. Furthermore, in the learning of the neural network 210, the configuration of the neural network 210 may be changed (for example, units may be added or deleted) without adjusting the weight W, and also both the adjustment of the weight W and the change of the configuration may be performed. In a case in which the neural network 210 is a multi-layer neural network apparatus, learning may be performed individually in each layer.

Generation of Weight Image and Useful Image

The weight image generating unit 203 images the weight W in the neural network 210 to generate a weight image group formed of weight images.

Figure 13:
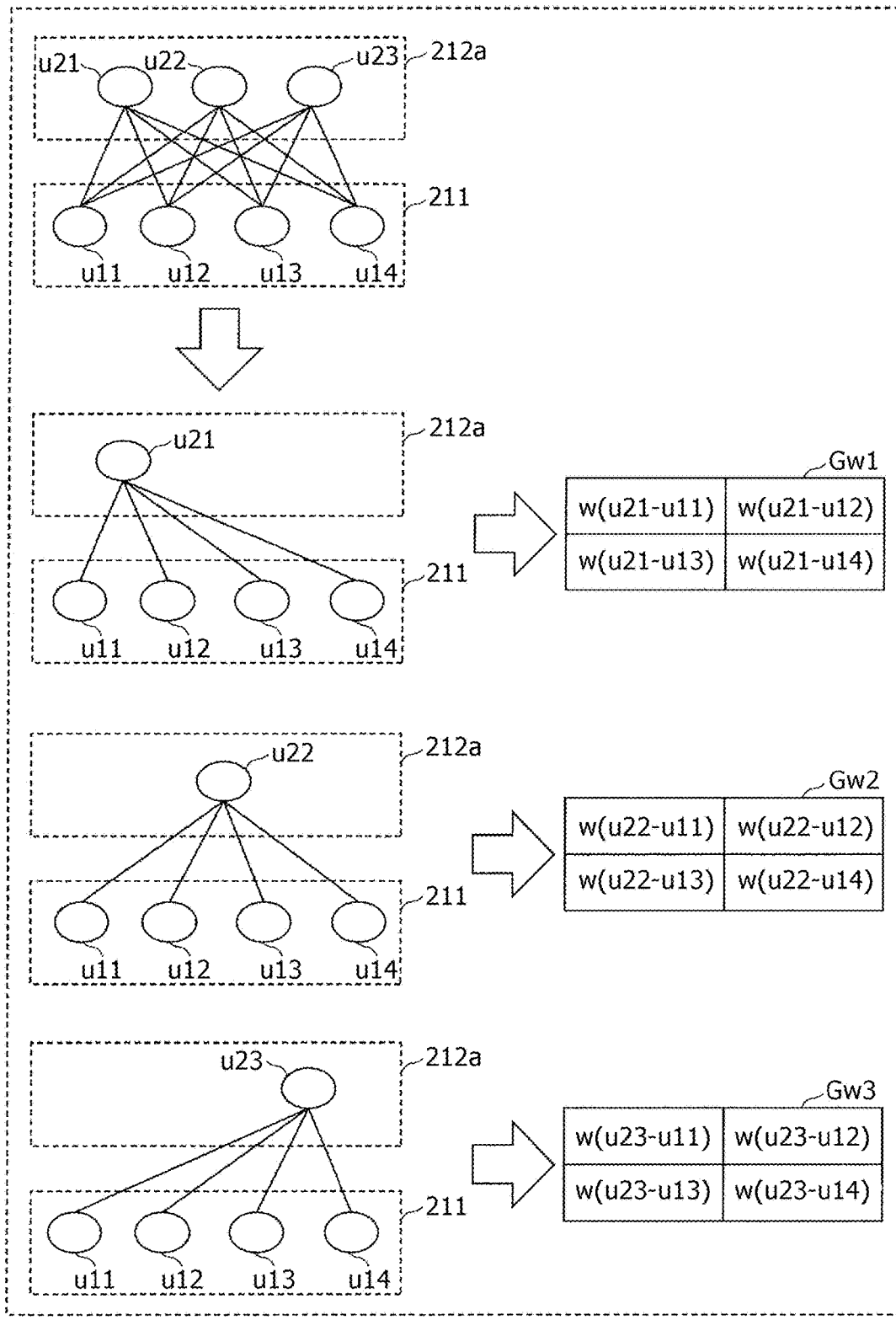
FIG. 13 illustrates an example of processing for generating a weight image group in the second embodiment.

FIG. 13 illustrates an example of processing for generating the weight image group. First, the weight image generating unit 203 acquires the input layer 211 of the neural network 210 and the hidden layer 212a that is connected to the input layer 211 by weight from the neural network 210.

Subsequently, the weight image generating unit 203 decomposes the weights of the units in the hidden layer 212a. That is, the weight image generating unit 203 generates a weight group Gw1 formed of weights used for calculation in a unit u21 in the hidden layer 212a, a weight group Gw2 formed of weights used for calculation in a unit u22 in the hidden layer 212a, and a weight group Gw3 formed of weights used for calculation in a unit u23 in the hidden layer 212a. The weight group Gw1 is formed of weights w(u21-u11), w(u21-u12), w(u21-u13), and w(u21-u14) that connect the unit u21 in the hidden layer 212a to units u11, u12, u13, and u14 in the input layer 211. The weight group Gw2 is formed of weights w(u22-u11), w(u22-u12), w(u22-u13), and w(u22-u14) that connect the unit u22 in the hidden layer 212a to the units u11, u12, u13, and u14 in the input layer 211. The weight group Gw3 is formed of weights w(u23-u11), w(u23-u12), w(u23-u13), and w(u23-u14) that connect the unit u23 in the hidden layer 212a to the units u11, u12, u13, and u14 in the input layer 211.

Subsequently, for each of these weight groups Gw1 to Gw3, the weight image generating unit 203 arranges the weights w included in the weight group as pixels in an image to generate a weight image. For example, the unit u11 in the input layer 211 corresponds to an upper left pixel in an image, the unit u12 corresponds to an upper right pixel in the image, the unit u13 corresponds to a lower left pixel in the image, and the unit u14 corresponds to a lower right pixel in the image.

At this time, the weight image generating unit 203 arranges the weights w included in the weight group Gw1 at the positions of the pixels corresponding to the units in the input layer 211. That is, the weight image generating unit 203 arranges the weights w(u21-u11), w(u21-u12), w(u21-u13), and w(u21-u14) at the positions of the pixels in the image corresponding to the units u11, u12, u13, and u14, respectively. Specifically, the weight image generating unit 203 arranges the weights w(u21-u11), w(u21-u12), w(u21-u13), and w(u21-u14) at the upper left, the upper right, the lower left, and the lower right in the image. Thus, a weight image including the weights w arranged two-dimensionally as pixel values is generated. The weight image generating unit 203 holds the weight image generated in the above manner.

Similarly, the weight image generating unit 203 arranges the weights w included in the weight group Gw2 at the positions of the pixels corresponding to the units in the input layer 211. That is, the weight image generating unit 203 arranges the weights w(u22-u11), w(u22-u12), w(u22-u13), and w(u22-u14) at the positions of the pixels in the image corresponding to the units u11, u12, u13, and u14, respectively. Specifically, the weight image generating unit 203 arranges the weights w(u22-u11), w(u22-u12), w(u22-u13), and w(u22-u14) at the upper left, the upper right, the lower left, and the lower right in the image. Thus, a weight image including the weights w arranged two-dimensionally as pixel values is generated. The weight image generating unit 203 holds the weight image generated in the above manner.

Similarly, the weight image generating unit 203 arranges the weights w included in the weight group Gw3 at the positions of the pixels corresponding to the units in the input layer 211. That is, the weight image generating unit 203 arranges the weights w(u23-u11), w(u23-u12), w(u23-u13), and w(u23-u14) at the positions of the pixels in the image corresponding to the units u11, u12, u13, and u14, respectively. Specifically, the weight image generating unit 203 arranges the weights w(u23-u11), w(u23-u12), w(u23-u13), and w(u23-u14) at the upper left, the upper right, the lower left, and the lower right in the image. Thus, a weight image including the weights w arranged two-dimensionally as pixel values is generated. The weight image generating unit 203 holds the weight image generated in the above manner.

Although the input layer 211 in the neural network 210 includes four units for simplicity of the description in the examples illustrated in FIGS. 11 to 13, the number of units may correspond to the number of pixels of an electrophoretic image Ei. For example, the number of units included in the input layer 211 is equal to the number of pixels of the electrophoretic image Ei. In addition, although each weight w is set as a pixel value in the generation of the weight image, the weight w may be different from the pixel value, and a value corresponding to the weight w may be set as the pixel value. That is, a value calculated from a function including the weight w as a variable may be set as the pixel value. In addition, the pixel value may be a luminance or chrominance.

In the weight image generated in the above manner, a pixel corresponding to a protein that is useful for the neural network 210 to identify a disease by using the electrophoretic image Ei has a large weight. For example, that pixel has a large pixel value, specifically, a high luminance. In contrast, in this weight image, a pixel corresponding to a protein that is not useful to identify the disease has a small weight. For example, that pixel has a small pixel value, specifically, a low luminance.

The useful image generating unit 204 calculates an average of weight images generated in the above manner, to generate a useful image.

FIG. 14 illustrates examples of the weight images and an example of the useful image.

For example, as illustrated in FIG. 14, the weight image generating unit 203 generates weight images Wi1 to Wi3 in which pixels having a large weight are white and in which pixels having a small weight are black. Specifically, the weight image generating unit 203 generates the weight image Wi1 based on the weight group Gw1, the weight image Wi2 based on the weight group Gw2, and the weight image Wi3 based on the weight group Gw3. In these weight images Wi1 to Wi3, for example, pixels corresponding to proteins that are useful to identify a disease such as sepsis have a large pixel value, and pixels corresponding to proteins that are not useful have a small pixel value. That is, in the weight images Wi1 to Wi3, spots corresponding to useful proteins are clearly shown.

From these weight images Wi1 to Wi3, the useful image generating unit 204 generates a single useful image Mi. In this embodiment, the useful image generating unit 204 obtains through calculation an average image of the weight images Wi1 to Wi3 to generate the useful image Mi. That is, the useful image generating unit 204 averages pixel values of pixels at identical positions in the one or more weight images included in the weight image group to generate the useful image Mi. Specifically, the useful image generating unit 204 calculates an average of pixels included in each pixel group formed of pixels at identical positions in the weight images Wi1 to Wi3 to generate the useful image Mi.

Each of the weight images Wi1 to Wi3 is generated by using some weights w among the weights w between the input layer 211 and the hidden layer 212a in the neural network 210. Thus, in some cases, protein considered to be useful may differ in the weight images Wi1 to Wi3. Accordingly, a user needs to visually check all of these weight images Wi1 to Wi3 in order to find the useful protein. However, according to this embodiment, since the useful image generating unit 204 generates the useful image Mi, the user can visually check the proteins at a time that are determined to be useful by the neural network 210, by using the single useful image Mi. In addition, as in the weight images Wi1 to Wi3, the spots corresponding to the useful proteins are clearly shown in the useful image Mi.

FIGS. 15A to 15C each illustrate a specific example of the weight images.

In each of the weight images, as illustrated in FIG. 15A, weights extracted from the neural network 210 are arranged two-dimensionally. For example, each of the weights is an integer from 0 to 255 and is used as a pixel value (specifically, luminance). Accordingly, as illustrated in FIG. 15B, the weight image includes brighter or whiter pixels for larger weights and darker or blacker pixels for smaller weights. In such a weight image, an aggregation of pixels that are brighter or whiter than peripheral pixels appears as a spot corresponding to the above-described useful protein. In a case in which the number of weights extracted from the neural network 210 is large, such as 1500×1500, spots do not seem to be aggregations of blocks as illustrated in FIG. 15B but seem to be a pattern as illustrated in FIG. 15C.

Image Display Example

FIGS. 16A to 16E each illustrate an example of an image displayed on the display 911 by the display processing unit 205.

Figure 16A:
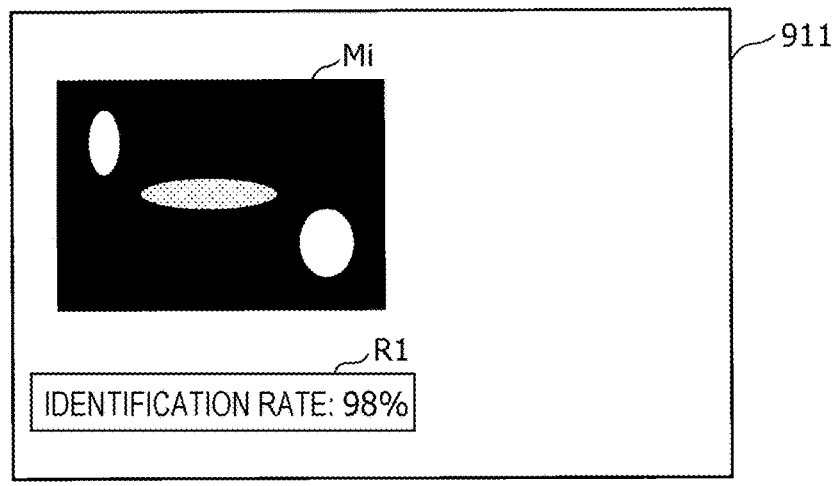
FIG. 16A illustrates an example of an image displayed on a display by a display processing unit in the second embodiment.

The display processing unit 205 obtains the useful image Mi from the useful image generating unit 204 and causes the display 911 to display the useful image Mi as illustrated in FIG. 16A. At this time, the display processing unit 205 causes the display 911 to display, not only the useful image Mi, but also the first identification rate obtained from the identification unit 202. The first identification rate is displayed in an identification rate display box R1 as "Identification Rate: 98%", for example.

As described above, in electrophoretic images Ei of the respective patients, a protein corresponding to a pixel at a specific position is common to all the patients. Thus, once the pixel is specified, the protein corresponding to the pixel is uniquely determined. As in the electrophoretic images Ei, also in the useful image Mi, once a pixel is specified, the protein corresponding to the pixel is uniquely determined. That is, the above-described correspondence table is also applicable to the useful image Mi.

Figure 16B:
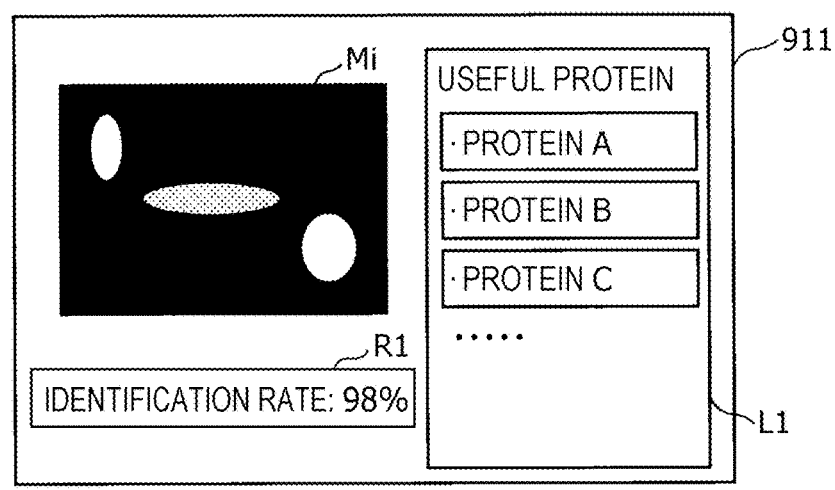
FIG. 16B illustrates another example of an image displayed on the display by the display processing unit in the second embodiment.

Accordingly, as illustrated in FIG. 16B, the display processing unit 205 may cause the display 911 to display a useful protein list L1. The useful protein list L1 illustrates information (e.g., names) of proteins corresponding to pixels included in the respective spots appearing in the useful image Mi.

That is, the display processing unit 205 in this embodiment makes a list of information of proteins corresponding to the respective spots appearing in the useful image Mi to generate the useful protein list L1. Then, the display processing unit 205 causes the display 911 to display the useful protein list L1 together with the useful image Mi. For example, the display processing unit 205 uses the above-described correspondence table to generate the useful protein list L1.

Thus, a user does not have to additionally search for the information of proteins corresponding to the respective spots appearing in the useful image Mi.

In addition, in response to a selection of any one spot from among the one or more spots appearing in the useful image Mi, or a selection of any one piece of information from the useful protein list L1, the display processing unit 205 in this embodiment selects a single useful protein corresponding to the selected spot or the selected piece of information as a selected protein.

Figure 16C:
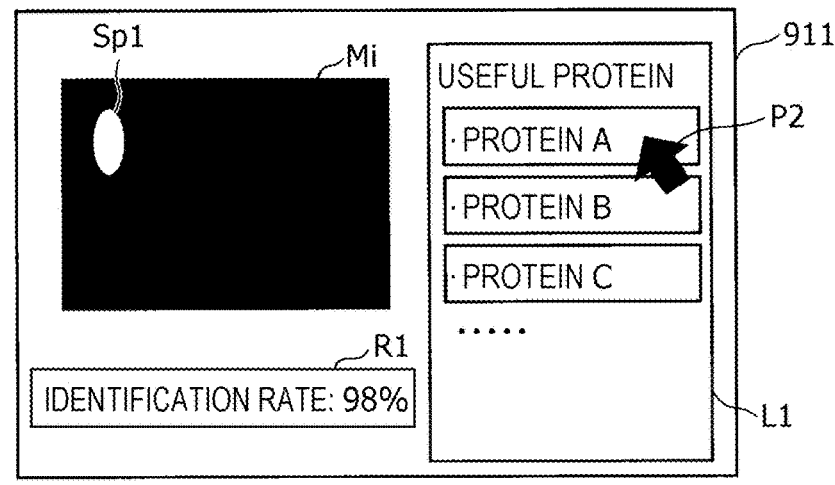
FIG. 16C illustrates another example of an image displayed on the display by the display processing unit in the second embodiment.

That is, as illustrated in FIG. 16C, in accordance with a user operation on the selection unit 913, the display processing unit 205 moves a pointer P2 displayed on the display 911. Then, in accordance with a user operation on the selection unit 913, the display processing unit 205 may select the name of protein indicated by the pointer P2. For example, "Protein A" is selected as the name of protein. Thus, the protein named "Protein A" is selected as a selected protein. In this case, the display processing unit 205 searches for spots other than the spot Sp1 corresponding to the protein named "Protein A" by using the above-described correspondence table and deletes the found spots from the useful image Mi.

Figure 16D:
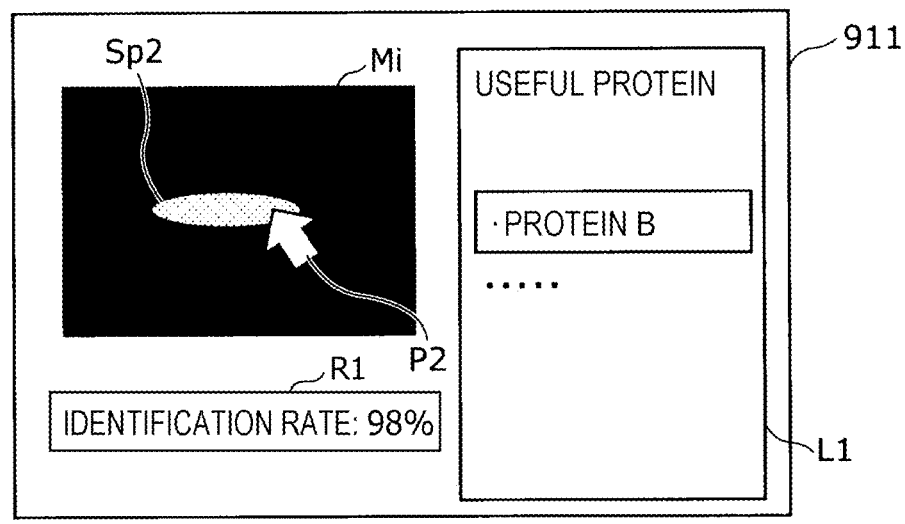
FIG. 16D illustrates another example of an image displayed on the display by the display processing unit in the second embodiment.

In addition, as illustrated in FIG. 16D, in accordance with a user operation on the selection unit 913, the display processing unit 205 moves, on the useful image Mi, the pointer P2 displayed on the display 911. Then, in accordance with a user operation on the selection unit 913, the display processing unit 205 may select a spot indicated by the pointer P2. For example, a spot Sp2 is selected. Thus, a protein corresponding to the spot Sp2 is selected as a selected protein. In this case, the display processing unit 205 deletes spots other than the selected spot Sp2 from the useful image Mi. Furthermore, the display processing unit 205 searches for the name of the selected protein corresponding to the spot Sp2 by using the above-described correspondence table. As a result, the display processing unit 205 finds "Protein B" as the name of the selected protein corresponding to the spot Sp2. Then, in the useful protein list L1, the display processing unit 205 causes "Protein B" to be displayed and deletes the names of the other proteins. As a result, the spot Sp2 appears in the useful image Mi, and the name "Protein B" is displayed in the useful protein list L1.

Thus, it is possible to check the position of the spot corresponding to the protein that is useful to identify a disease in the useful image Mi in relation to the information (i.e., name or the like) of the protein. Note that the display of the name of the selected protein illustrated in FIG. 16D is an example, and the display processing unit 205 may display the name in a different manner. For example, when the spot is selected in the useful image Mi, the display processing unit 205 may change the color, font size, or the like of the name of the selected protein corresponding to the spot in the useful protein list L1 to emphasize the name.

Figure 16E:
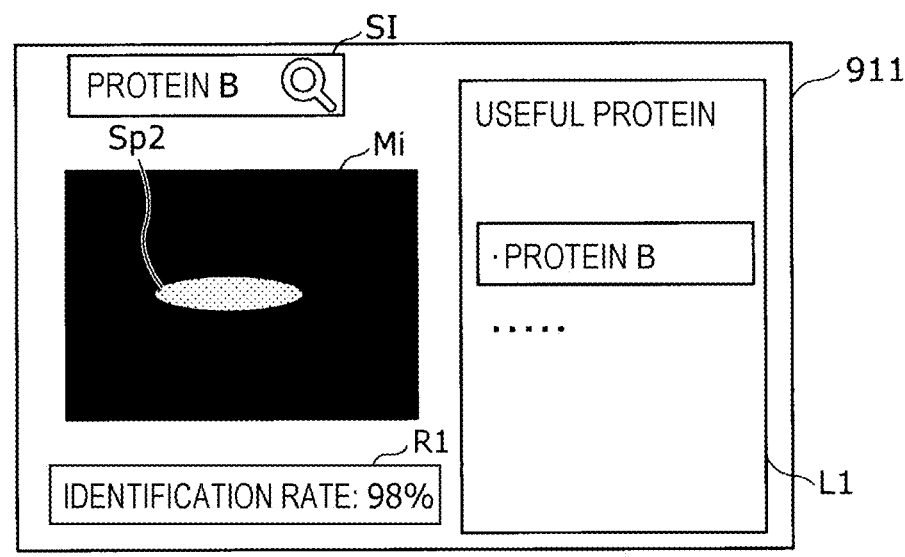
FIG. 16E illustrates another example of an image displayed on the display by the display processing unit in the second embodiment.

Alternatively, as illustrated in FIG. 16E, the display processing unit 205 may cause the display 911 to display a search icon Si. In this case, upon the name of protein being input into the search icon SI, the display processing unit 205 treats the protein corresponding to the name as a selected protein. That is, the display processing unit 205 searches for a spot corresponding to the selected protein in the useful image Mi by using the above-described correspondence table and deletes spots other than the spot from the useful image Mi. For example, upon "Protein B" being input into the search icon SI, spots other than the spot Sp2 corresponding to the selected protein named "Protein B" are deleted from the useful image Mi. In addition, the display processing unit 205 may cause the name "Protein B" of the selected protein to be displayed in the useful protein list L1 and may delete the names of the other proteins. Thus, the spot Sp2 appears in the useful image Mi, and the name "Protein B" is displayed in the useful protein list L1.

Even in such display, as in the example illustrated in FIG. 16D, it is possible to check the position of the spot corresponding to the protein that is useful to identify a disease in the useful image Mi in relation to the information (i.e., name or the like) of the protein.

Overall Operation

Figure 17:
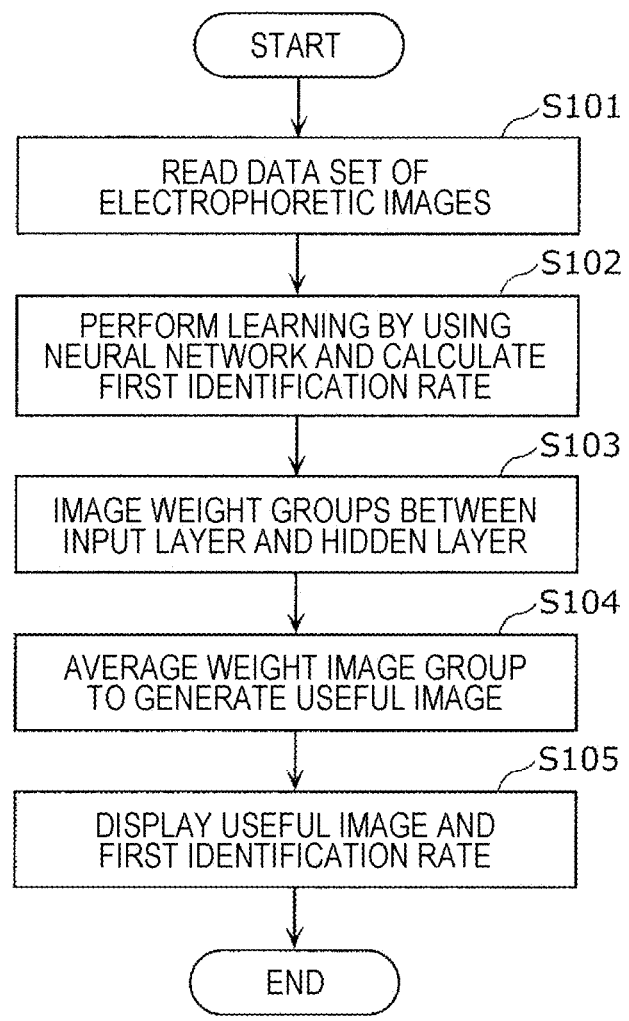
FIG. 17 is a flowchart illustrating an overall processing operation of the display control apparatus according to the second embodiment.

FIG. 17 is a flowchart illustrating an overall processing operation of the display control apparatus 200 according to this embodiment.

[Step S101]

First, the identification unit 202 of the display control apparatus 200 reads a data set of electrophoretic images Ei from the memory 201.

[Step S102]

Subsequently, by using the data set and the neural network 210, the identification unit 202 learns the relationship between the electrophoretic images Ei and a disease and calculates a disease identification rate of the data set in the neural network 210 as a first identification rate.

[Step S103]

Subsequently, the weight image generating unit 203 images weight groups between the input layer 211 and the hidden layer 212a in the neural network 210 to generate a weight image group formed of one or more weight images.

[Step S104]

Subsequently, the useful image generating unit 204 averages the weight image group to generate a useful image Mi.

[Step S105]

Subsequently, the display processing unit 205 causes the display 911 to display both the useful image Mi generated in step S104 and the first identification rate calculated in step S102.

As described above, the display control apparatus 200 according to this embodiment can present the protein that is useful to identify a disease together with the identification rate. Accordingly, it is possible to present the effectiveness of the protein without the need to make a biomarker by selecting the target protein.

Third Embodiment

A display control apparatus according to a third embodiment has the function of the display control apparatus 200 according to the second embodiment and also displays an identification rate obtained when a spot of a selected protein is used, as a second identification rate.

Overall Configuration

Figure 18:
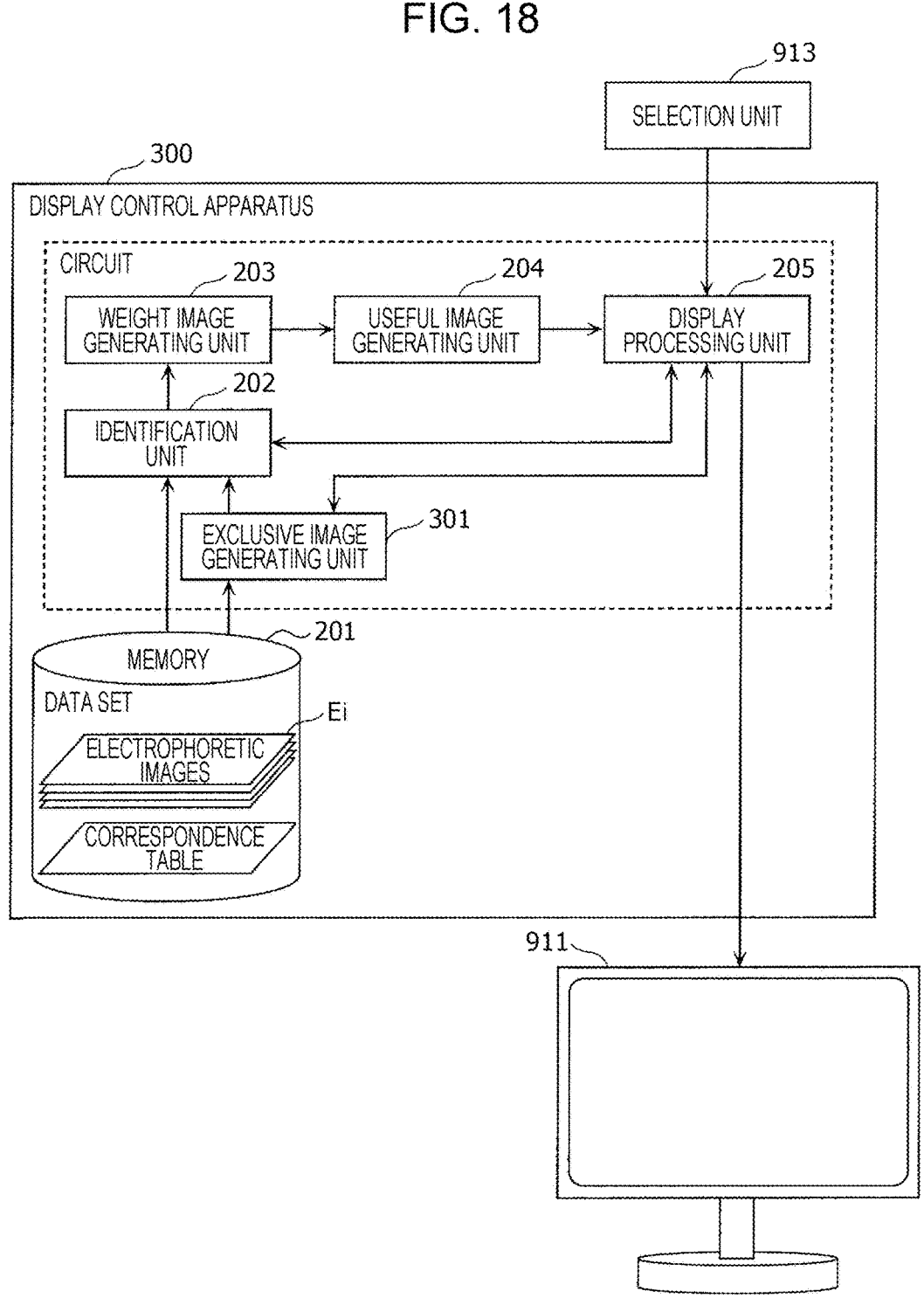
FIG. 18 is a block diagram illustrating an example of a functional configuration of a display control apparatus according to a third embodiment.

FIG. 18 is a block diagram illustrating an example of a functional configuration of a display control apparatus 300 according to this embodiment. Note that, among components of the display control apparatus 300 illustrated in FIG. 18, the same components as those in the second embodiment are denoted by the same reference numerals as those in the second embodiment, and therefore a specific description will be omitted.

As illustrated in FIG. 18, the display control apparatus 300 according to this embodiment includes the components in the second embodiment and further includes an exclusive image generating unit 301. Note that the identification unit 202, the weight image generating unit 203, the useful image generating unit 204, the display processing unit 205, and the exclusive image generating unit 301 may be configured from one or more circuits.

The exclusive image generating unit 301 excludes, from the respective electrophoretic images Ei included in a data set in the memory 201, spots not corresponding to the selected protein to generate exclusive images.

In addition, by inputting the exclusive images into the neural network 210, the identification unit 202 in this embodiment further calculates an identification rate of the exclusive images in the neural network 210 as a second identification rate. The second identification rate is an identification rate obtained when the selected protein is used.

The display processing unit 205 causes the display 911 to display the second identification rate.

Example of Generation of Exclusive Image

Figure 19:
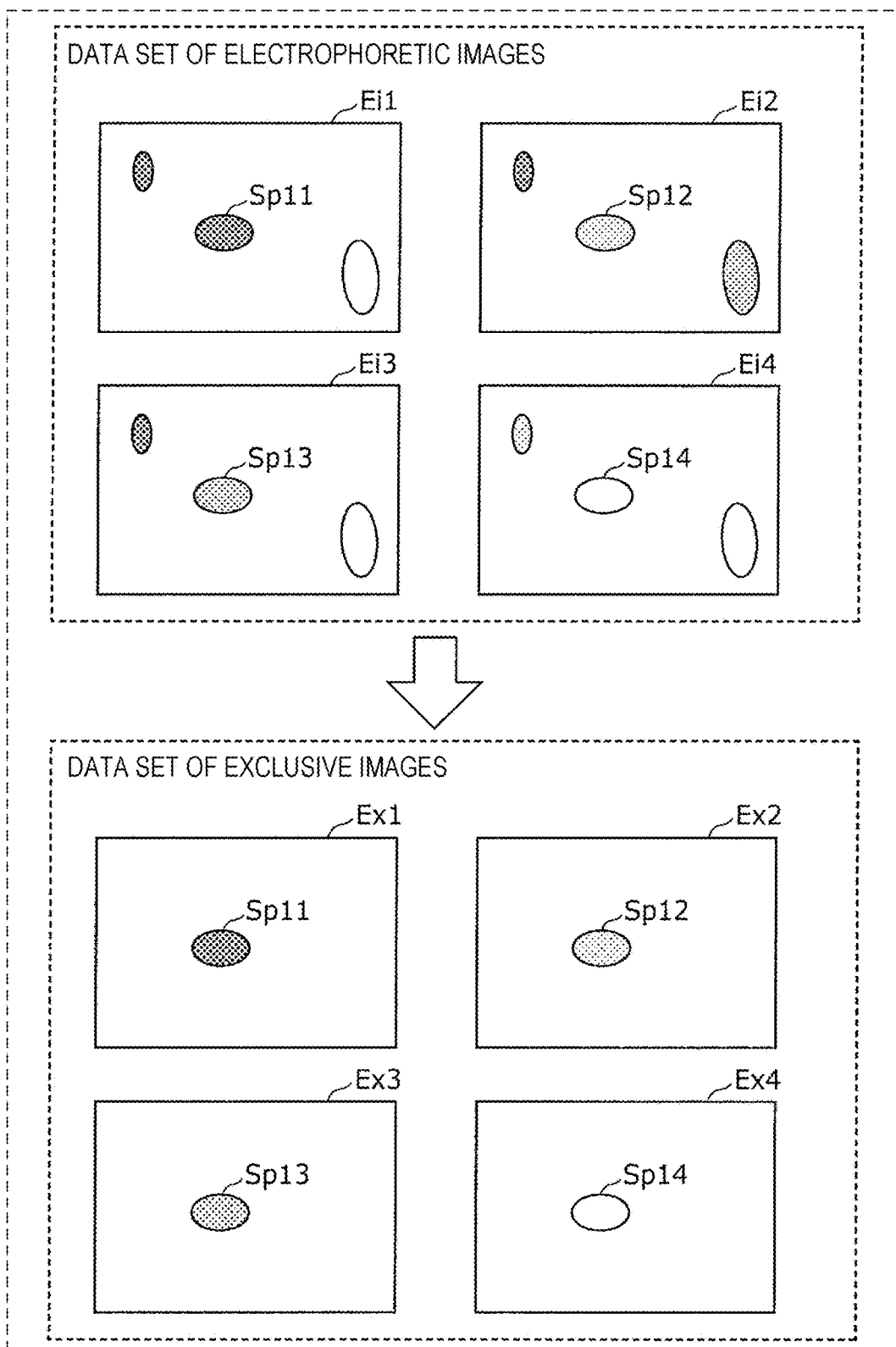
FIG. 19 illustrates examples of exclusive images generated by an exclusive image generating unit in the third embodiment.

FIG. 19 illustrates examples of exclusive images generated by the exclusive image generating unit 301.

As illustrated in FIG. 19, the exclusive image generating unit 301 reads a data set including electrophoretic images Ei1, Ei2, Ei3, and Ei4 from the memory 201. In addition, the exclusive image generating unit 301 obtains, through the display processing unit 205, information (e.g., name) of the selected protein, which is a useful protein selected in accordance with a user operation on the selection unit 913. Subsequently, on the basis of the information and the correspondence table, the exclusive image generating unit 301 excludes spots other than the spot corresponding to the selected protein form each of the electrophoretic images Ei1, Ei2, Ei3, and Ei4. For example, the spot corresponding to the selected protein is as follows: a spot Sp11 in the electrophoretic image Ei1, a spot Sp12 in the electrophoretic image Ei2, a spot Sp13 in the electrophoretic image Ei3, and a spot Sp14 in the electrophoretic image Ei4. Note that each of the spots Sp11, Sp12, Sp13, and Sp14 is located at the same position in the electrophoretic images.

In this case, the exclusive image generating unit 301 excludes spots other than the spot Sp11 from the electrophoretic image Ei1 to generate an exclusive image Ex1. Similarly, the exclusive image generating unit 301 excludes spots other than the spot Sp12 from the electrophoretic image Ei2 to generate an exclusive image Ex2, and excludes spots other than the spot Sp13 from the electrophoretic image Ei3 to generate an exclusive image Ex3. In addition, the exclusive image generating unit 301 excludes spots other than the spot Sp14 from the electrophoretic image Ei4 to generate an exclusive image Ex4.

Image Display Example

Figure 20A:
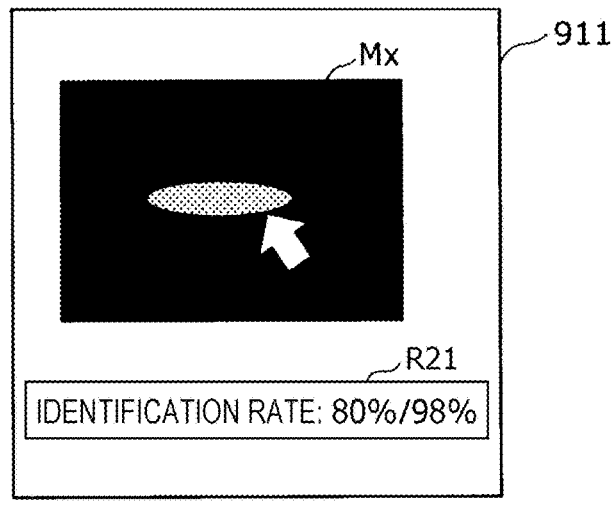
FIG. 20A illustrates an example of an image displayed on the display by the display processing unit in the third embodiment.
Figure 20B:
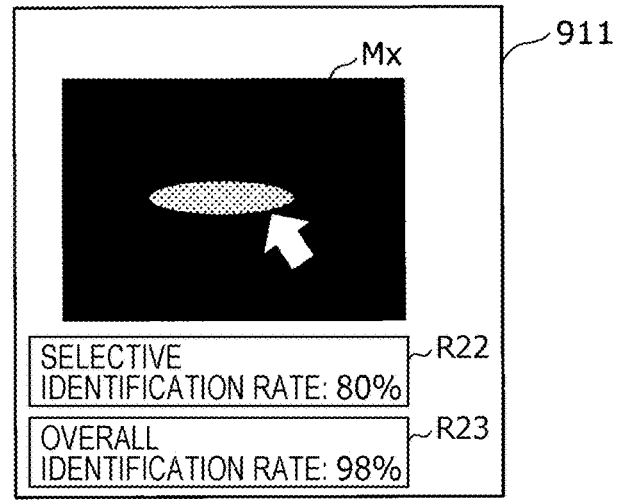
FIG. 20B illustrates an example of an image displayed on the display by the display processing unit in the third embodiment.
Figure 20C:
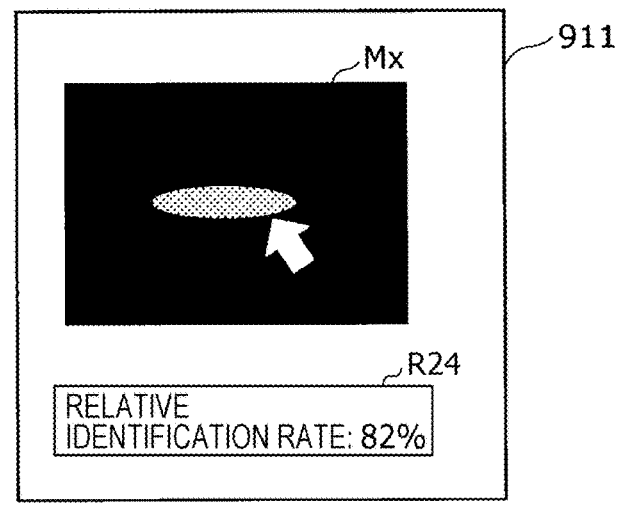
FIG. 20C illustrates an example of an image displayed on the display by the display processing unit in the third embodiment.

FIGS. 20A to 20C each illustrate an example of an image displayed on the display 911 by the display processing unit 205.

The exclusive image generating unit 301 obtains through calculation an average image of the exclusive images Ex1, Ex2, Ex3, and Ex4 generated in the above manner to generate an exclusive useful image Mx. The display processing unit 205 causes the display 911 to display the exclusive useful image Mx as illustrated in FIG. 20A.

Here, by inputting the exclusive images Ex1, Ex2, Ex3, and Ex4 into the neural network 210, the identification unit 202 calculates the identification rate of the exclusive images in the neural network 210 as the second identification rate. As illustrated in FIG. 20A, the display processing unit 205 causes the display 911 to display the second identification rate together with the exclusive useful image Mx. The second identification rate is "80%", for example, and is displayed in an identification rate display box R21 so as to be compared with the above-described first identification rate (e.g., "98%"). In the example illustrated in FIG. 20A, the second identification rate is displayed as a numerator of a fraction. That is, the numerator of the fraction is the second identification rate, which is the identification rate obtained when the selected protein is used, and the denominator of the fraction is the first identification rate, which is the identification rate obtained when all the useful proteins are used.

Note that the second identification rate may be displayed in any manner without limitation to the example illustrated in FIG. 20A. For example, as illustrated in FIG. 20B, the first identification rate and the second identification rate may be displayed in an identification rate display box R23 and an identification rate display box R22, respectively, which are independent of each other, instead of using a fraction. That is, the second identification rate, which is the identification rate obtained when the selected protein is used, is displayed as "Selective Identification Rate: 80%", for example, in the identification rate display box R22. In addition, the first identification rate, which is the identification rate obtained when all the useful proteins are used, is displayed as "Overall Identification Rate: 98%", for example, in the identification rate display box R23. In this manner, both the first identification rate and the second identification rate may be displayed independently of each other.

As illustrated in FIG. 20C, the display processing unit 205 may alternatively calculate a relative identification rate by dividing the second identification rate by the first identification rate and may cause the display 911 to display the relative identification rate together with the exclusive useful image Mx. For example, the relative identification rate is displayed as "Relative Identification Rate: 82%" in an identification rate display box R24.

The display processing unit 205 may also cause the display 911 to display the useful protein list L1 together as in the second embodiment.

Overall Configuration

FIG. 21 is a flowchart illustrating an overall processing operation of the display control apparatus 300 according to this embodiment. In the processing operation illustrated in the flowchart of FIG. 21, the second identification rate, which is the identification rate obtained when the selected protein is used, is displayed.

[Step S100]

As in the second embodiment, the display control apparatus 300 performs processing in S101 to S105 illustrated in FIG. 17 to cause the display 911 to display the useful image Mi.

[Step S201]

Subsequently, in accordance with a user operation on the selection unit 913, the display processing unit 205 of the display control apparatus 300 selects one spot from among the spots appearing in the useful image Mi. Thus, a useful protein corresponding to the spot is selected as a selected protein. That is, the display processing unit 205 refers to the position of the selected spot and the above-described correspondence table to select the protein corresponding to the spot as the selected protein.

Note that the useful image Mi is not an image of proteins in the actual case, but is obtained by imaging the weights in the neural network 210. However, since the weights in the neural network 210 correspond to proteins in a one-to-one relationship, a selection of a spot (i.e., weight) in the useful image Mi can be regarded as a selection of a protein.

In a case in which the useful protein list L1 is displayed as illustrated in FIG. 16C, in accordance with a user operation on the selection unit 913, the display processing unit 205 may select a name included in the useful protein list L1. Thus, the protein with the name is selected as the selected protein. In addition, in a case in which the search icon SI is displayed as illustrated in FIG. 16E, the display processing unit 205 may select the protein corresponding to a name that is input into the search icon SI as the selected protein.

[Step S202]

Subsequently, the exclusive image generating unit 301 excludes spots of proteins other than the selected protein from each of the electrophoretic images Ei included in a data set of the memory 201 to generate a data set formed of exclusive images. That is, as illustrated in FIG. 19, the exclusive image generating unit 301 excludes spots other than the spot Sp11 from the electrophoretic image Ei1 to generate the exclusive image Ex1. Similarly, the exclusive image generating unit 301 generates the exclusive image Ex2 from the electrophoretic image Ei2, the exclusive image Ex3 from the electrophoretic image Ei3, and the exclusive image Ex4 from the electrophoretic image Ei4.

[Step S203]

Subsequently, the identification unit 202 inputs the generated data set of the exclusive images into the neural network 210. At this time, re-learning of the neural network 210 may be performed by using steepest descent or the like.

[Step S204]

In response to the input in step S203, the identification unit 202 calculates the identification rate of the data set of the exclusive images in the neural network 210 as the second identification rate.

[Step S205]

The display processing unit 205 displays both the first identification rate calculated in step S100 and the second identification rate calculated in step S204.

In the above manner, the display control apparatus 300 according to the third embodiment displays the identification rate obtained when the selected protein is used. This enables determination of the most useful protein by selecting proteins one by one if there are proteins that are useful to identify a disease. Typically, a biomarker is used to check the amount of a single protein that has appeared. Accordingly, to determine the most useful protein by using a biomarker, it has been necessary to make biomarkers suitable for the respective proteins. However, in this embodiment, the protein that is the most useful to identify a disease can be easily determined without making such a biomarker.

Modification of Third Embodiment

Although the exclusive images are generated in order to display the identification rate obtained when the selected protein is used, as the second identification rate in the above-described embodiment, the second identification rate may be displayed without generating the exclusive images. For example, the identification unit 202 may set weights corresponding to proteins other than the selected protein, among the weights in the neural network 210, to zero.

That is, among the weights in the neural network 210, the identification unit 202 sets one or more weights not corresponding to the selected protein to zero to change the neural network 210.

Note that each pixel of an electrophoretic image Ei corresponds to one or more proteins as illustrated in the above-described correspondence table. In addition, each unit included in the input layer 211 in the neural network 210 corresponds to the pixel of the electrophoretic image Ei. Accordingly, each unit included in the input layer 211 in the neural network 210 corresponds to one or more proteins. Thus, in a case in which the neural network 210 is changed as in the above case, among the units included in the input layer 211 in the neural network 210, the identification unit 202 determines one or more units not corresponding to the selected protein. Then, for each of the determined one or more units, the identification unit 202 sets the weights between the unit and units in the hidden layer 212a to zero.

In addition, by inputting the electrophoretic images Ei included in the data set in the memory 201 into the changed neural network 210, the identification unit 202 calculates an identification rate of the data set in the changed neural network 210 as the second identification rate. The display processing unit 205 causes the display 911 to display the second identification rate.

This enables calculation and display of the second identification rate obtained when the selected protein is used, without using the exclusive image generating unit 301.

Fourth Embodiment

A display control apparatus according to a fourth embodiment displays a combination of proteins for obtaining an identification rate higher than the second identification rate. This combination is a combination of the selected protein and a protein other than the selected protein.

Overall Configuration

Figure 22:
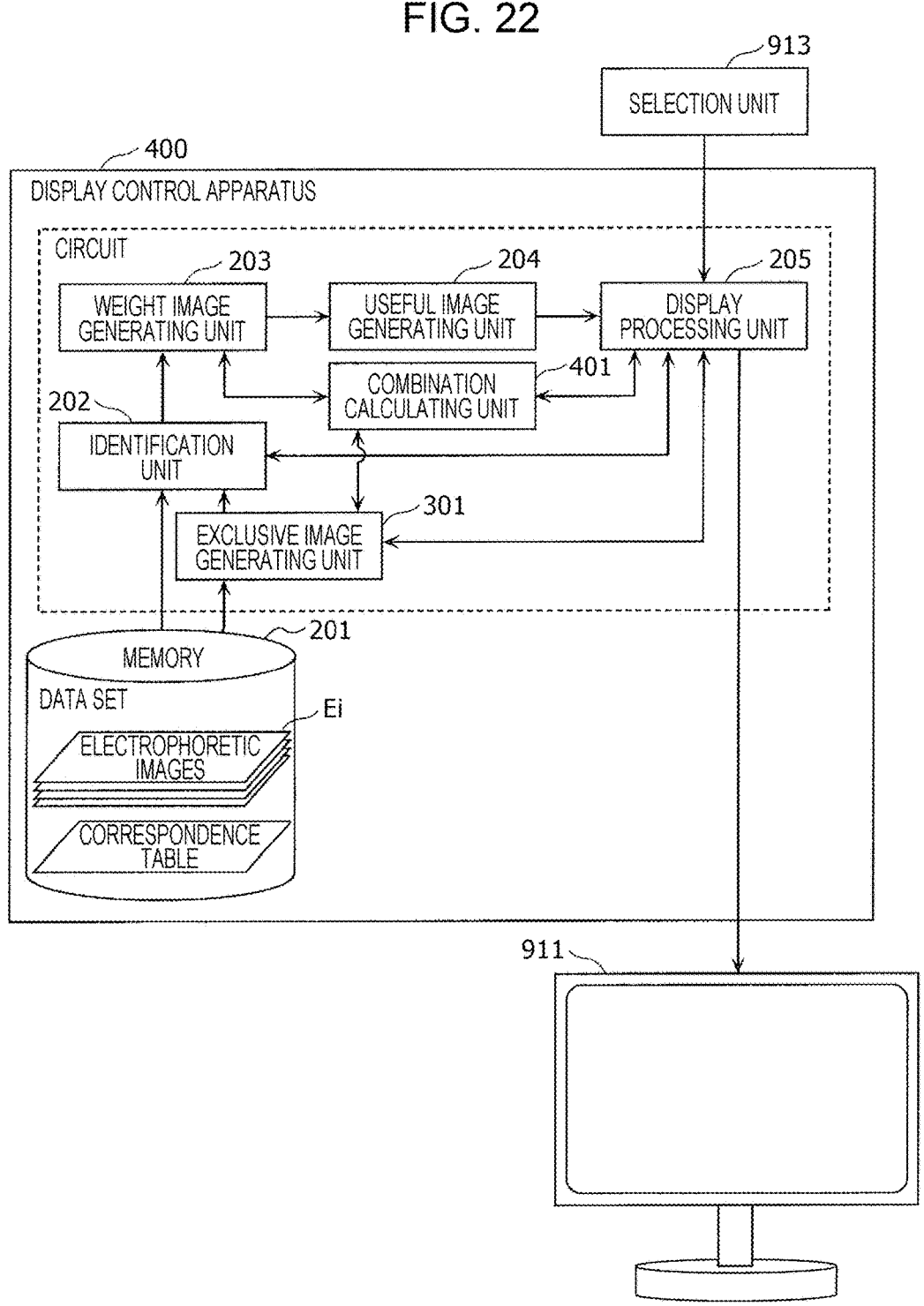
FIG. 22 is a block diagram illustrating an example of a functional configuration of a display control apparatus according to a fourth embodiment.

FIG. 22 is a block diagram illustrating an example of a functional configuration of a display control apparatus 400 according to this embodiment. Note that, among components of the display control apparatus 400 illustrated in FIG. 22, the same components as those in the second or third embodiment are denoted by the same reference numerals as those in the second or third embodiment, and therefore a specific description will be omitted.

As illustrated in FIG. 22, the display control apparatus 400 according to this embodiment includes the components in the third embodiment and further includes a combination calculating unit 401. Note that the identification unit 202, the weight image generating unit 203, the useful image generating unit 204, the display processing unit 205, the exclusive image generating unit 301, and the combination calculating unit 401 may be configured from one or more circuits.

By using a weight image group generated by the weight image generating unit 203, the combination calculating unit 401 finds a combination of proteins. That is, by combining proteins with a selected protein, which is a useful protein selected by a user operation on the selection unit 913, the combination calculating unit 401 finds a protein by which the identification rate is increased to be higher than the second identification rate.

Specifically, for each of non-selected proteins, which are proteins other than the selected protein, the combination calculating unit 401 determines the number of weight images including a spot of the selected protein and spots of the non-selected proteins from the weight image group. That is, the combination calculating unit 401 counts the number of weight images. Then, in the descending order of the number of weight images, the combination calculating unit 401 extracts, from the above-described non-selected proteins, N (N is an integer greater than or equal to 1) non-selected proteins from a first non-selected protein to an N-th selected protein. By combining the N non-selected proteins extracted in this manner with the selected protein, the identification rate is increased to be higher than the second identification rate.

The display processing unit 205 causes the display 911 to display information of each of the extracted N non-selected proteins.

Hereinafter, each of the N non-selected proteins to be combined with the selected protein is referred to as a combination protein.

Processing of Combination Calculating Unit

Figure 23:
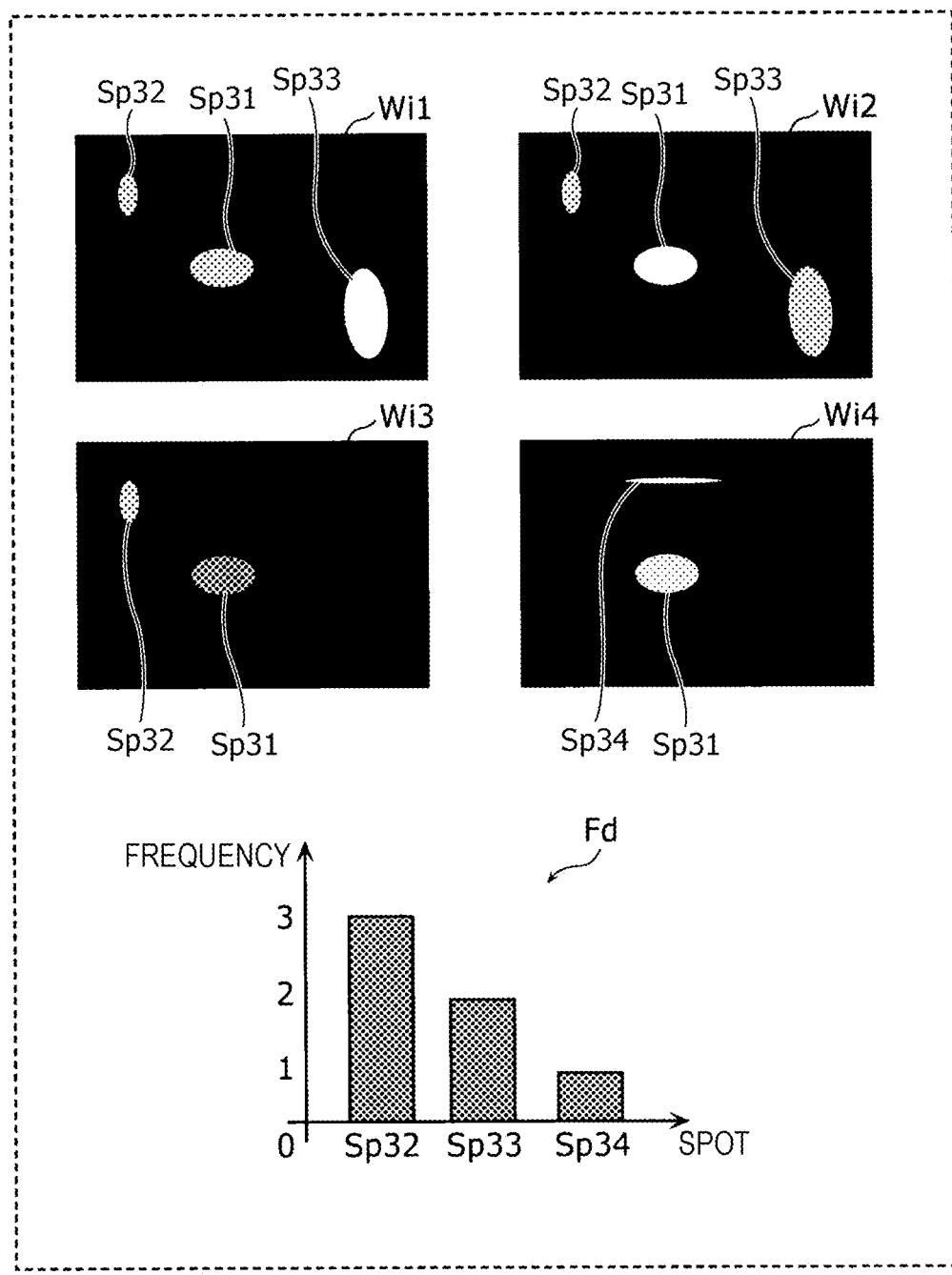
FIG. 23 illustrates an example of processing for extracting a combination protein in the fourth embodiment.

FIG. 23 illustrates an example of processing for extracting a combination protein.

From each of weight images Wi1, Wi2, Wi3, and Wi4 included in the weight image group generated by the weight image generating unit 203, the combination calculating unit 401 selects a spot Sp31 corresponding to the selected protein. Specifically, the combination calculating unit 401 selects the spot Sp31 formed of pixels having a weight (i.e., pixel value) greater than or equal to a threshold Th. For example, if a possible weight is −1 to +1, the threshold Th is Th=0. Alternatively, the threshold Th is Th=α×maxW, where maxW is a maximum weight and α is a parameter such as 0.9. This enables detection of an image having a large weight of the selected protein (i.e., the spot Sp31) from the weight image group.

In addition, for each of the non-selected proteins other than the selected protein, the combination calculating unit 401 counts the number of weight images including spots of the non-selected proteins together with the spot of the selected protein from the weight image group. Note that the spots of the non-selected proteins are also formed of, for example, pixels having a weight greater than or equal to the above-described threshold Th. In other words, the combination calculating unit 401 counts the frequency of weights other than the weight corresponding to the selected protein from the weight image group.

For example, as illustrated in FIG. 23, the frequencies of the spot Sp31 corresponding to the selected protein and a spot Sp32 that appears in the same weight image are three, the frequency of a spot Sp 33 is two, and the frequency of a spot Sp34 is one. These frequencies are represented as a frequency distribution Fd.

Subsequently, by using the above-described frequency distribution Fd, the combination calculating unit 401 selects N spots in higher levels in the descending order of the frequency. For example, in a case in which N=1, by using the frequency distribution Fd, the spot Sp32 is selected. Thus, a non-selected protein corresponding to the spot Sp32 is extracted as the combination protein from among the non-selected proteins.

Calculation of Third Identification Rate Using Combination

The exclusive image generating unit 301 reads a data set formed of electrophoretic images Ei from the memory 201. The exclusive image generating unit 301 also obtains information (e.g., name) of the selected protein and information of N combination proteins from the combination calculating unit 401. Subsequently, on the basis of the information and the above-described correspondence table, the exclusive image generating unit 301 excludes spots other than a specific spot from each of the electrophoretic images Ei. The specific spot includes the spot corresponding to the selected protein and the spots corresponding to the N combination proteins. This generates a data set of exclusive images in which the spot of the selected protein and N spots in higher levels in the descending order of the frequency remain.

By inputting the generated data set formed of the exclusive images into the neural network 210, the identification unit 202 calculates a third identification rate. The third identification rate is higher than the second identification rate.

Image Display Example

Figure 24A:
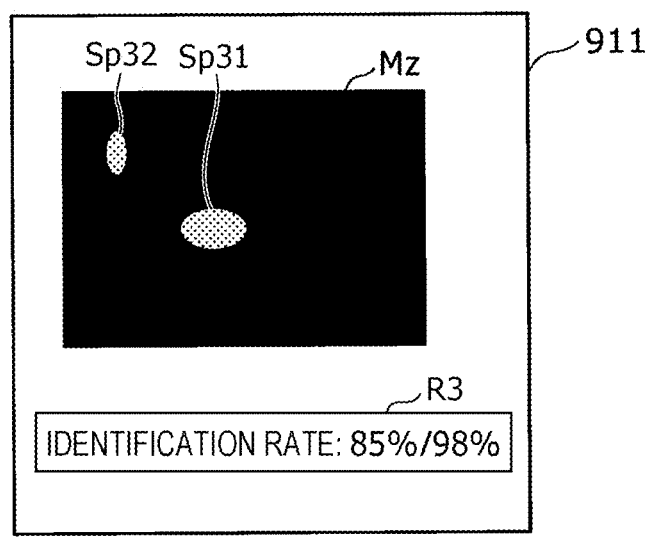
FIG. 24A illustrates an example of an image displayed on the display by the display processing unit in the fourth embodiment.
Figure 24B:
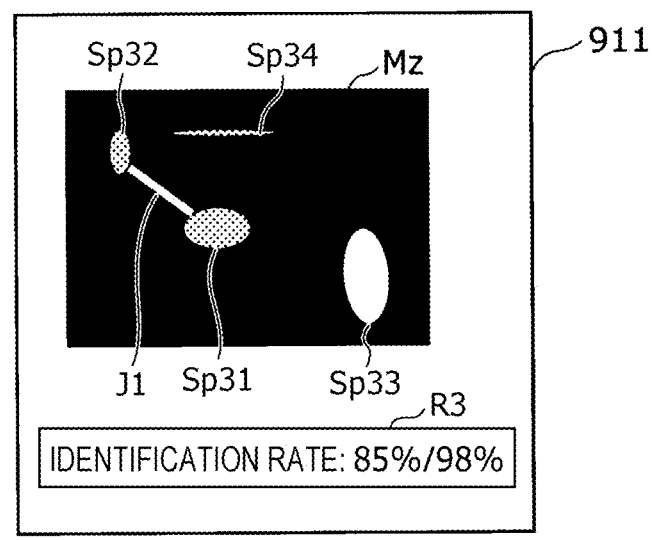
FIG. 24B illustrates an example of an image displayed on the display by the display processing unit in the fourth embodiment.

FIGS. 24A and 24B each illustrate an example of an image displayed on the display 911 by the display processing unit 205.

The display processing unit 205 obtains the information (e.g., name) of the selected protein and the information of the N combination proteins from the combination calculating unit 401. Subsequently, on the basis of the information, as illustrated in FIG. 24A, the display processing unit 205 generates a combination useful image Mz in which the spot Sp31 of the selected protein and the spot Sp32 of the N combination proteins (single combination protein in the example of FIGS. 24A and 24B) remain. That is, the display processing unit 205 excludes spots other than the spot Sp31 corresponding to the selected protein and the spot Sp32 corresponding to the combination protein from the useful image Mi to generate the combination useful image Mz.

In addition, the display processing unit 205 obtains the third identification rate from the identification unit 202. Then, as illustrated in FIG. 24A, the display processing unit 205 causes the display 911 to display the combination useful image Mz and the third identification rate. The third identification rate is "85%", for example, and is displayed in an identification rate display box R3 so as to be compared with the above-described first identification rate (e.g., "98%"). In the example illustrated in FIG. 24A, the third identification rate is displayed as a numerator of a fraction. That is, the numerator of the fraction is the third identification rate, which is the identification rate obtained when the combination of proteins is used, and the denominator of the fraction is the first identification rate, which is the identification rate obtained when all the useful proteins are used.

Alternatively, as illustrated in FIG. 24B, the display processing unit 205 may generate the combination useful image Mz without excluding spots from the useful image Mi. In this case, the display processing unit 205 superimposes, on the useful image Mi, a linear object J1 that joins the spot Sp31 of the selected protein and the spot Sp32 of the N combination proteins (single combination protein in the example of FIGS. 24A and 24B) to each other. This generates the combination useful image Mz illustrating the combination of the spot Sp31 of the selected protein and the spot Sp32 of the combination protein.

Note that the display of the combination of the spot of the selected protein and the spots of the N combination proteins is not limited to the example illustrated in FIG. 24, and the combination may be displayed in any manner as long as the combination is explicitly illustrated.

Overall Operation

Figure 25:
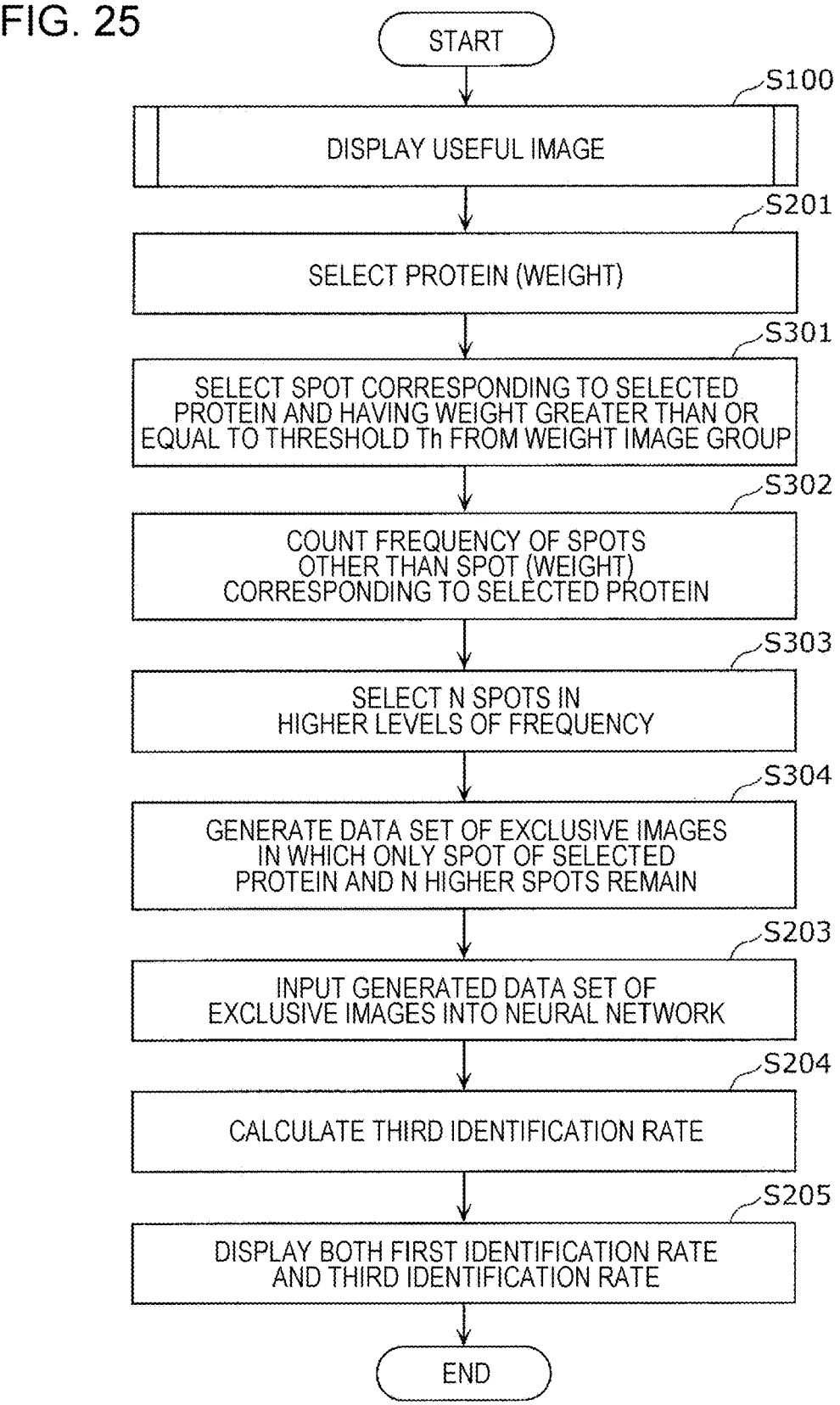
FIG. 25 is a flowchart illustrating an overall processing operation of the display control apparatus according to the fourth embodiment.

FIG. 25 is a flowchart illustrating an overall processing operation of the display control apparatus 400 according to this embodiment. In the processing operation illustrated in the flowchart of FIG. 25, the combination of proteins and the third identification rate, which is the identification rate obtained when the combination is used, are displayed.

[Step S100]

As in the second embodiment, the display control apparatus 400 performs processing in S101 to S105 illustrated in FIG. 17 to cause the display 911 to display the useful image Mi.

[Step S201]

Subsequently, as in the third embodiment, in accordance with a user operation on the selection unit 913, the display processing unit 205 of the display control apparatus 400 selects one spot from among the spots appearing in the useful image Mi. Thus, a useful protein corresponding to the spot is selected as a selected protein.

[Step S301]

Subsequently, the combination calculating unit 401 selects the spot corresponding to the selected protein from each of the weight images included in the weight image group. This spot is an image formed of pixels having a pixel value corresponding to a weight greater than or equal to the threshold Th.

[Step S302]

Subsequently, for each of the non-selected proteins other than the selected protein, the combination calculating unit 401 counts the number of weight images including spots of the non-selected proteins together with spot of the selected protein from the weight image group. The number of weight images counted in this manner is the frequency of the spots of the non-selected proteins.

[Step S303]

Subsequently, the combination calculating unit 401 selects N spots in higher levels in the descending order of the frequency.

[Step S304]

Subsequently, the exclusive image generating unit 301 excludes spots other than the spot of the selected protein and the spots of the N combination proteins from each of the electrophoretic images Ei. This generates a data set of exclusive images in which the spot of the selected protein and the N spots in higher levels in the descending order of the frequency remain.

[Step S203]

Subsequently, as in the third embodiment, the identification unit 202 inputs the generated data set of the exclusive images into the neural network 210.

[Step S204]

As in the third embodiment, in response to the input in step S203, the identification unit 202 calculates the identification rate of the data set of the exclusive images in the neural network 210 as the third identification rate.

[Step S205]

The display processing unit 205 displays both the first identification rate calculated in step S100 and the third identification rate calculated in step S204.

In the above manner, in this embodiment, the combination protein for increasing the identification rate is found by using the weight image group. This corresponds to evaluation of the combination of proteins that are necessary to fire each unit in an intermediate layer (i.e., hidden layer) in the neural network 210. Accordingly, a protein having a larger weight in accordance with the selected protein has a high correlation with the selected protein for the units in the intermediate layer. The neural network 210 determines whether there is a disease on the basis of the combination of the fired units in the intermediate layer. Thus, by combining the protein having a larger weight in accordance with the selected protein with the selected protein, the disease identification rate can be increased.

Other Embodiments

Although the display control apparatuses according to the above embodiments of the present disclosure have been described above, the present disclosure is not limited to these embodiments.

For example, the display control apparatus according to any of the above embodiments may be realized by using a computer.

Figure 26:
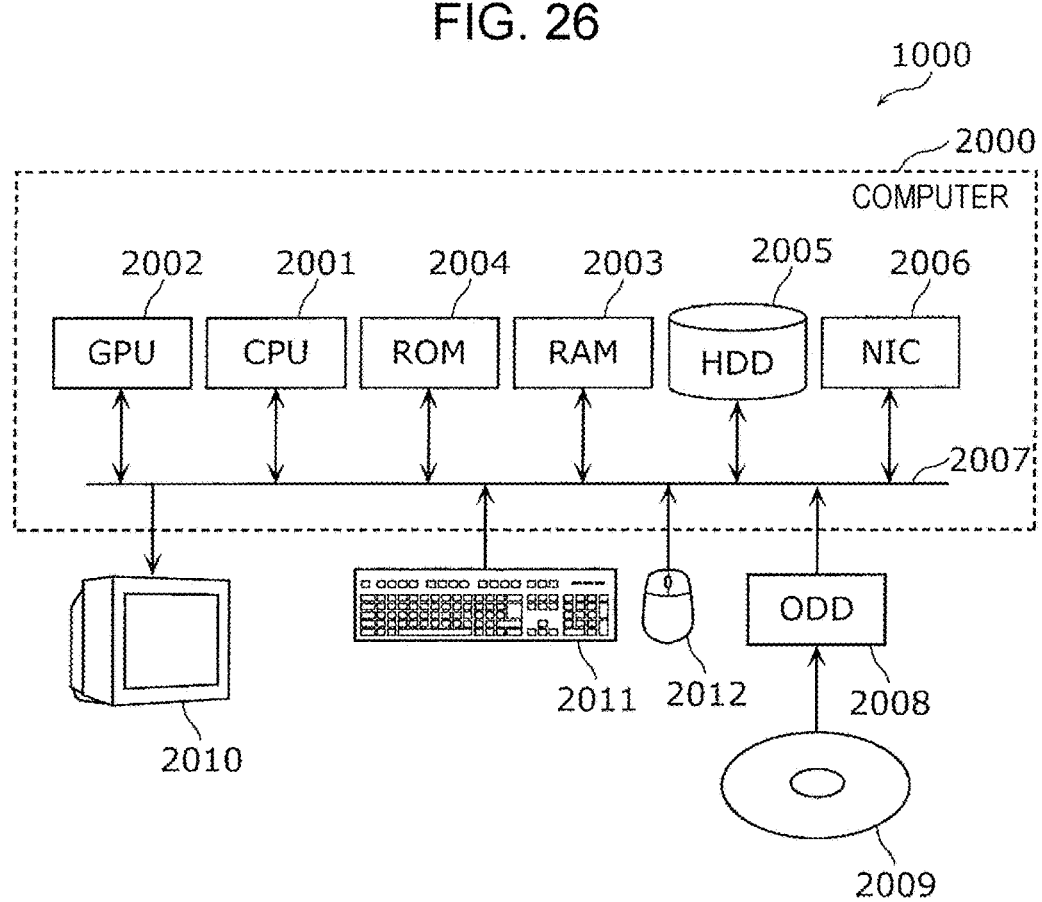
FIG. 26 is a block diagram illustrating a hardware configuration for realizing the display control apparatus according to an embodiment.

FIG. 26 is a block diagram illustrating a hardware configuration for realizing the display control apparatus according to an embodiment.

A display control apparatus 1000 includes a computer 2000, a keyboard 2011 and a mouse 2012 for instructing the computer 2000, a display 2010 for presenting information such as a computation result of the computer 2000, and an optical disk drive (ODD) 2008 for reading a program to be executed by the computer 2000.

The program to be executed by the display control apparatus 1000 is stored in a computer-readable optical storage medium 2009 and is read by the ODD 2008. Alternatively, the program is read by a network interface controller (NIC) 2006 through a computer network.

The computer 2000 includes a central processing unit (CPU) 2001, a read only memory (ROM) 2004, a random access memory (RAM) 2003, a hard disk drive (HDD) 2005, the NIC 2006, and a bus 2007.

The computer 2000 may further include a graphical processing unit (GPU) 2002 for high-speed computation.

The CPU 2001 and the GPU 2002 execute the program read through the ODD 2008 or the NIC 2006. The ROM 2004 stores a program or data necessary for the operation of the computer 2000. The RAM 2003 stores data such as parameters used when the program is executed. The HDD 2005 stores programs, data, or the like. The NIC 2006 communicates with another computer via the computer network. The bus 2007 connects the CPU 2001, the ROM 2004, the RAM 2003, the HDD 2005, the NIC 2006, the display 2010, the keyboard 2011, the mouse 2012, and the ODD 2008 to one another. Note that the keyboard 2011, the mouse 2012, and the ODD 2008 connected to the computer 2000 may be detached when, for example, the display 2010 serves as a touch panel and/or when the NIC 2006 is used.

In addition, some or all of the components of the display control apparatus 1000 may be configured from a single system large scale integration (LSI). The system LSI is a super multi-function LSI manufactured by configuring component units on a single chip and is specifically a computer system including a microprocessor, a ROM, a RAM, and the like. The RAM stores a computer program. By the microprocessor operating in accordance with the computer program, the system LSI implements the function.

Furthermore, some or all of the components may be configured from an IC card or a single module that is attachable to and detachable from each apparatus. The IC card or module is a computer system configured from a microprocessor, a ROM, a RAM, or the like. The IC card or module may include the above-described super multi-function LSI. By the microprocessor operating in accordance with the computer program, the IC card or module implements the function. The IC card or module may be tamper resistant.

The present disclosure may also be the methods described above. The present disclosure may also include computer programs that realize these methods by using a computer and may also include digital signal based on the computer program.

Furthermore, the present disclosure may include a computer-readable non-transitory storage medium such as a flexible disk, a hard disk, a CD-ROM, a magneto-optical (MO) disk, a digital versatile disc (DVD), a DVD-ROM, a DVD-RAM, a Blu-ray (registered trademark) (BD) Disc, or a semiconductor memory storing the above computer program or digital signal. The present disclosure may further include the digital signal stored in such a non-transitory storage medium.

The present disclosure may also be implemented by transmitting the above computer program or digital signal via a tele communication line, a wireless communication line, a wired communication line, or a network typified by an Internet, data transmission, or the like.

In addition, another independent computer system may implement the present disclosure by receiving the above program or digital signal stored in any of the above non-transitory storage mediums or by receiving the above programs or digital signal via the above network or the like.

Figure 27:
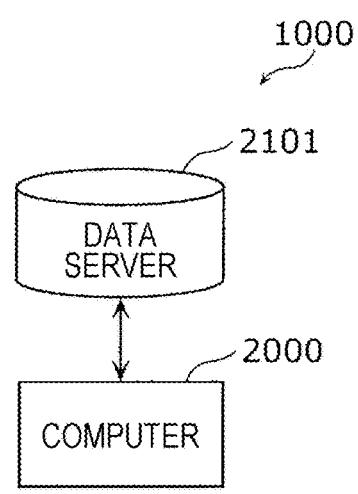
FIG. 27 is a block diagram illustrating another hardware configuration for realizing the display control apparatus according to an embodiment.

FIG. 27 is a block diagram illustrating another hardware configuration for realizing the display control apparatus according to an embodiment.

In the present disclosure, as illustrated in FIG. 27, a data server 2101 may be additionally constructed in addition to the computer 2000, and data to be stored may be stored in a memory or the like of the data server 2101, and the computer 2000 may read information thereof via the above network or the like. In addition, the computer 2000 that reads the information from the data server 2101 may be a single computer or multiple computers. In a case in which multiple computers are used as the computers 2000, each of the computers 2000 may perform part of the processing of the display control apparatus 1000.

In addition, the display control apparatus according to any of the above embodiments may be configured as a server. In this case, the display control apparatus receives signals from the input device 912 or the selection unit 913 via a communication network such as the Internet and controls display of the display 911 in accordance with signals.

In the present disclosure, some or all of the units and devices, or some or all of components in the functional block diagrams illustrated in FIGS. 1, 9, 18, and 22, may be implemented by one or more electronic circuits including a semiconductor apparatus, a semiconductor integrated circuit (IC), or a large scale integration (LSI). The LSI or IC may be integrated on a single chip or may be configured by a combination of chips. For example, functional blocks other than storage elements may be integrated on a single chip. Although the terms LSI and IC are used here, the names differ depending on the degree of integration and may be a system LSI, a very large scale integration (VLSI), or an ultra large scale integration (ULSI). A field Programmable Gate Array (FPGA) that can be programmed after manufacture of an LSI or a reconfigurable logic device in which the connection relationship inside the LSI can be reconfigured or in which the circuit division inside the LSI can be set up can be used for the same purpose.

Furthermore, some or all of functions or operations of the units, the apparatuses, or some of the apparatuses can be implemented by software processing. In this case, software is stored in one or more non-transitory recording mediums such as a ROM, an optical disk, and a hard disk drive, and when the software is executed by a processor, the software causes the processor and a peripheral device to execute a specific function of the software. The system or apparatus may include one or more non-transitory recording mediums storing the software, the processor, and a necessary hardware device such as an interface.

Although the display control apparatus according to one or more aspects has been described above on the basis of the embodiments, the present disclosure is not limited to the embodiments. The one or more aspects may include various modifications of the embodiments that a person skilled in the art will arrive at and modes constructed by combining components in different embodiments without departing from the spirit of the present disclosure.

The present disclosure enables presentation of proteins that are useful to identify a disease on the basis of an identification rate and is applicable to, for example, biomarker development, a diagnosis assistance apparatus based on protein analysis, and the like.

What is claimed is:

1. A display control apparatus, comprising:
a memory that stores an electrophoretic image including pixels and useful protein information showing relationships between the pixels and useful proteins, each of the pixels corresponding to one or more useful proteins included in the useful proteins; and
a circuit that
(a1) obtains the electrophoretic image and the useful protein information from the memory,
(a2) causes a display to display the electrophoretic image as a first display image,
(a3) receives a selection of a first pixel from among the pixels included in the electrophoretic image displayed on the display,
(a4) obtains, on the basis of the useful protein information, (i) one or more first useful proteins that are included in the useful proteins and correspond to the first pixel and (ii) one or more second useful proteins that are included in the useful proteins and correspond to one or more second pixels, a length between the first pixel and each of the one or more second pixels being less than or equal to a first length, and
(a5) causes the display to display the electrophoretic image, the one or more first useful proteins, and the one or more second useful proteins as a second display image.

2. The display control apparatus according to claim 1, wherein, if the one or more first useful proteins include a third useful protein and a fourth useful protein in the (a4), the circuit causes one or more third pixels and one or more fourth pixels to be displayed in an emphasized manner in the electrophoretic image in the second display image, the one or more third pixels corresponding to the third useful protein, the one or more fourth pixels corresponding to the fourth useful protein.

3. The display control apparatus according to claim 1, wherein the circuit
(a6) receives a selection of any of the one or more first useful proteins or the one or more second useful proteins while the second display image is displayed, and
(a7) causes the display to display one or more fifth pixels in an emphasized manner in the electrophoretic image in the second display image, the one or more fifth pixels corresponding to the useful protein whose selection has been received.

4. The display control apparatus according to claim 1, wherein, between the (a2) and the (a3), the circuit
(a8) receives an enlarge operation of the electrophoretic image or a reduce operation of the electrophoretic image centering one or more pixels among the pixels in the first display image, and
(a9) on the basis of the received enlarge operation or the received reduce operation, changes a magnifying power of the electrophoretic image in the first display image and causes the display to display the electrophoretic image with the changed magnifying power, and
wherein, after the selection of the first pixel has been received in the (a3), at least in the (a4) or the (a5), the magnifying power of the electrophoretic image is not changed in accordance with the enlarge operation or the reduce operation.

5. A display control apparatus, comprising:
a memory that includes a data set formed of electrophoretic images; and
a circuit that
(b1) learns a relationship between the electrophoretic images and a disease by using the data set and a neural network,
(b2) images weights in the neural network obtained from a result of the learning of the relationship to generate a weight image group formed of one or more weight images,
(b3) calculates a disease identification rate of the data set in the neural network as a first identification rate,
(b4) generates a useful image by using the weight image group, and
(b5) causes a display to display both the useful image and the first identification rate,
wherein the useful image includes pixels,
wherein the pixels include a pixel i having a pixel value i and corresponding to a useful protein i, a pixel j having a pixel value j and corresponding to a useful protein j, and a pixel k having a pixel value k and corresponding to a useful protein k, and
wherein, if the useful protein i is most useful to identify the disease and the useful protein k is least useful to identify the disease among the useful protein i, the useful protein j, and the useful protein k, the pixel value i>the pixel value j>the pixel value k is set, or the pixel value i<the pixel value j<the pixel value k is set.

6. The display control apparatus according to claim 5, wherein in the (b4), the useful image is generated by averaging pixel values of pixels at identical positions in the one or more weight images included in the weight image group.

7. The display control apparatus according to claim 5, wherein the circuit further
(b6) makes a list of information of proteins corresponding to one or more spots appearing in the useful image to generate a useful protein list, and
causes, in the (b5), the display to display the useful protein list together with the useful image.

8. The display control apparatus according to claim 7, wherein the circuit further
(b7) selects, in response to a selection of any one spot from among the one or more spots appearing in the useful image, or a selection of any one piece of information from the useful protein list, a single protein corresponding to the selected spot or the selected piece of information as a selected protein.

9. The display control apparatus according to claim 8, wherein the circuit further
(b8) sets one or more weights not corresponding to the selected protein among the weights in the neural network to zero to change the neural network,
(b9) inputs the electrophoretic images included in the data set into the changed neural network to calculate an identification rate of the data set in the changed neural network as a second identification rate, and
(b10) causes the display to display the second identification rate.

10. The display control apparatus according to claim 8, wherein the circuit further
(b11) excludes, from the respective electrophoretic images included in the data set, spots not corresponding to the selected protein to generate exclusive images, (b12) inputs the exclusive images into the neural network to calculate an identification rate of the exclusive images in the neural network as a second identification rate, and (b13) causes the display to display the second identification rate.

11. The display control apparatus according to claim 9, wherein the circuit further (b14) determines, for each of non-selected proteins, which are proteins other than the selected protein, the number of weight images including a spot of the selected protein and spots of the non-selected proteins from the weight image group, (b15) extracts, in a descending order of the number of weight images, from the non-selected proteins, N, which is an integer greater than or equal to 1, non-selected proteins from a first non-selected protein to an N-th non-selected protein, and (b16) causes the display to display information of each of the extracted N non-selected proteins.

12. The display control apparatus according to claim 1, wherein the useful proteins are useful to identify diseases.

13. A display control method for controlling display of a display by using a memory and a circuit, the memory storing an electrophoretic image including pixels and useful protein information showing relationships between the pixels and useful proteins, each of the pixels corresponding to one or more useful proteins included in the useful proteins, the method comprising:

by using the circuit, (a1) obtaining the electrophoretic image and the useful protein information from the memory;

(a2) causing a display to display the electrophoretic image as a first display image;

(a3) receiving a selection of a first pixel from among the pixels included in the electrophoretic image displayed on the display;

(a4) obtaining, on the basis of the useful protein information, (i) one or more first useful proteins that are included in the useful proteins and correspond to the first pixel and (ii) one or more second useful proteins that are included in the useful proteins and correspond to one or more second pixels, a length between the first pixel and each of the one or more second pixels being less than or equal to a first length; and (a5) causing the display to display the electrophoretic image, the one or more first useful proteins, and the one or more second useful proteins as a second display image.

14. The display control method according to claim 13, wherein the one or more first useful proteins include a third useful protein and a fourth useful protein in the (a4), and the circuit causes one or more third pixels and one or more fourth pixels to be displayed in an emphasized manner in the electrophoretic image in the second display image, the one or more third pixels corresponding to the third useful protein, the one or more fourth pixels corresponding to the fourth useful protein.

15. The display control method according to claim 13, further comprising:

by using the circuit, (a6) receiving a selection of any of the one or more first useful proteins or the one or more second useful proteins while the second display image is displayed; and (a7) causing the display to display one or more fifth pixels in an emphasized manner in the electrophoretic image in the second display image, the one or more fifth pixels corresponding to the useful protein whose selection has been received.

16. The display control method according to claim 13, further comprising:

between the (a2) and the (a3), by using the circuit, (a8) receiving an enlarge operation of the electrophoretic image or a reduce operation of the electrophoretic image centering one or more pixels among the pixels in the first display image; and (a9) on the basis of the received enlarge operation or the received reduce operation, changing a magnifying power of the electrophoretic image in the first display image and causing the display to display the electrophoretic image with the changed magnifying power, and wherein, after the selection of the first pixel has been received in the (a3), at least in the (a4) or the (a5), the magnifying power of the electrophoretic image is not changed in accordance with the enlarge operation or the reduce operation.

17. A display control method for controlling display of a display by using a memory and a circuit, the memory including a data set formed of electrophoretic images, the method comprising:

by using the circuit, (b1) learning a relationship between the electrophoretic images and a disease by using the data set and a neural network;

(b2) imaging weights in the neural network obtained from a result of the learning of the relationship to generate a weight image group formed of one or more weight images;

(b3) calculating a disease identification rate of the data set in the neural network as a first identification rate;

(b4) generating a useful image by using the weight image group; and (b5) causing the display to display both the useful image and the first identification rate, wherein the useful image includes pixels, wherein the pixels include a pixel i having a pixel value i and corresponding to a useful protein i, a pixel j having a pixel value j and corresponding to a useful protein j, and a pixel k having a pixel value k and corresponding to a useful protein k, and wherein, if the useful protein i is most useful to identify the disease and the useful protein k is least useful to identify the disease among the useful protein i, the useful protein j, and the useful protein k, the pixel value i>the pixel value j>the pixel value k is set, or the pixel value i<the pixel value j<the pixel value k is set.

18. A non-transitory computer-readable recording medium storing a program for causing a device including a processor to execute processing, the processing comprising:

by using the circuit, (a1) obtaining, from a memory storing an electrophoretic image including pixels and useful protein information showing relationships between the pixels and useful proteins, each of the pixels corresponding to one or more useful proteins included in the useful proteins, the electrophoretic image and the useful protein information;

(a2) causing a display to display the electrophoretic image as a first display image;

(a3) receiving a selection of a first pixel from among the pixels included in the electrophoretic image displayed on the display;

(a4) obtaining, on the basis of the useful protein information, (i) one or more first useful proteins that are included in the useful proteins and correspond to the first pixel and (ii) one or more second useful proteins that are included in the useful proteins and correspond to one or more second pixels, a length between the first pixel and each of the one or more second pixels being less than or equal to a first length; and (a5) causing the display to display the electrophoretic image, the one or more first useful proteins, and the one or more second useful proteins as a second display image.

\* \* \* \* \*